(12) United States Patent
Pereira Nascimento Costa et al.

(10) Patent No.: US 10,450,322 B2
(45) Date of Patent: Oct. 22, 2019

(54) LOW MOLECULAR WEIGHT DERIVATIVES OF CARBOXAMIDE HALOGENATED PORPHYRINS, NAMELY CHLORINS AND BACTERIOCHLORINS, AND THEIR APPLICATIONS THEREOF

(71) Applicants: LUZITIN, S.A., Coimbra (PT); UNIVERSIDADE DE COIMBRA, Coimbra (PT)

(72) Inventors: Goncalo Pereira Nascimento Costa, Coimbra (PT); Nuno Paulo Ferreira Goncalves, Coimbra (PT); Carlos Jorge Pereira Monteiro, Coimbra (PT); Artur Carlos Reis De Abreu, Povoa de Santa Iria (PT); Helder Tao Ferraz Cardoso Soares, Ermesinde (PT); Luis Gabriel Borges Rocha, Coimbra (PT); Fabio Antonio Schaberle, Coimbra (PT); Maria Miguens Pereira, Coimbra (PT); Luis Guilherme Da Silva Arnaut Moreira, Coimbra (PT)

(73) Assignees: LUZITIN, S.A., Coimbra (PT); UNIVERSIDADE DE COIMBRA, Coimbra (PT)

( * ) Notice: Subject to any disclaimer, the term of this patent is extended or adjusted under 35 U.S.C. 154(b) by 0 days.

(21) Appl. No.: 15/570,956

(22) PCT Filed: May 6, 2016

(86) PCT No.: PCT/IB2016/052606
§ 371 (c)(1),
(2) Date: Nov. 6, 2017

(87) PCT Pub. No.: WO2016/178191
PCT Pub. Date: Nov. 10, 2016

(65) Prior Publication Data
US 2018/0282344 A1 Oct. 4, 2018

(30) Foreign Application Priority Data
May 7, 2015 (PT) .................................... 108447

(51) Int. Cl.
| A61K 41/00 | (2006.01) |
| A61K 49/10 | (2006.01) |
| A61B 5/00 | (2006.01) |
| C07D 487/22 | (2006.01) |
| A61B 5/055 | (2006.01) |
| A61N 5/06 | (2006.01) |

(52) U.S. Cl.
CPC .......... *C07D 487/22* (2013.01); *A61B 5/0095* (2013.01); *A61B 5/055* (2013.01); *A61K 41/0028* (2013.01); *A61K 41/0071* (2013.01); *A61K 49/106* (2013.01); *A61N 5/062* (2013.01); *C07B 2200/07* (2013.01); *C07B 2200/09* (2013.01)

(58) Field of Classification Search
CPC ....... A61K 41/00; A61K 49/05; C07D 487/22
See application file for complete search history.

(56) References Cited

U.S. PATENT DOCUMENTS

2012/0289492 A1* 11/2012 Patel .................... A61K 31/555
514/185

FOREIGN PATENT DOCUMENTS

| WO | 2011099602 A1 | 8/2011 |
| WO | 2016051361 A1 | 4/2016 |

OTHER PUBLICATIONS

International Search Report and Written Opinion for International Application No. PCT/IB2016/052606 (11 Pages) (dated Sep. 20, 2016).

Takanami et al., "An efficient one-pot procedure for asymmetric bifunctionalization of 5,15-disubstituted porphyrins: a simple preparation of meso acyl-, alkoxycarbonyl-, and carbamoyl-substituted meso-formylporphyrins", Chem. Commun., 2009, No. 1, pp. 101-103.

* cited by examiner

*Primary Examiner* — Michael G. Hartley
*Assistant Examiner* — Jagadishwar R Samala
(74) *Attorney, Agent, or Firm* — Lucas & Mercanti, LLP

(57) ABSTRACT

The present invention relates to carboxamide halogenated porphyrin derivatives, in particular bacteriochlorin or chlorin, of formula (I) use of the same or a pharmaceutically acceptable salt thereof in photodynamic therapy, where the derivatives are able to detect and exhibit the presence of hyperproliferative disorders and, in the presence of an adequate lighting, to treat the same. The present invention also describes a pharmaceutical composition having the carboxamide halogenated porphyrin derivatives, in particular bacteria-chlorin or chlorin, of Formula (I) or a pharmaceutically acceptable salt thereof, for the treatment of cancer and/or microbial and/or viral infections, in humans or animals.

19 Claims, 8 Drawing Sheets

(IX)

(Xa) (Xb)

LOW MOLECULAR WEIGHT DERIVATIVES OF CARBOXAMIDE HALOGENATED PORPHYRINS, NAMELY CHLORINS AND BACTERIOCHLORINS, AND THEIR APPLICATIONS THEREOF

CROSS REFERENCE TO RELATED APPLICATION

This Application is a 371 of PCT/IB2016/052606 filed on May 6, 2016, which claims priority of Portuguese Application No. 108447 filed May 7, 2015, both of which are incorporated herein by reference.

TECHNICAL FIELD

The present application relates to new low-molecular weight carboxamide halogenated porphyrin derivatives, namely chlorin and bacteriochlorin derivatives, and their preparation process and use in photodynamic therapy.

BACKGROUND OF THE INVENTION

Photodynamic therapy (PDT) is a clinically approved treatment based on the administration of a photosensitizing molecule, its accumulation in the target tissue, and then illumination with light selectively absorbed by the photosensitizer. This selectivity is improved using photosensitizers that absorb light in the phototherapeutic window (650-850 nm), where tissues have higher optical penetration depths (e.g., $\delta$=2.3 mm at 750 nm) (1). The absorption of light leaves the photosensitizer in an electronically excited state that reacts with substrate molecules by electron transfer reactions with the formation of superoxide anion and hydroxyl radicals (type I reaction), or to transfer its energy to ground-state molecular oxygen generating singlet oxygen (type II reaction). These photogenerated reactive oxygen species (ROS) trigger biological mechanisms that make PDT an effective anti-cancer procedure (2).

The paradigm of PDT in the treatment of hyperproliferative disorders has been that stable dyes with a stronger absorption of light in the phototherapeutic window and with high ROS quantum yields ($\Phi_{ROS}$) should be better photosensitizers. Additionally, the development of PDT photosensitizers targeting Gram-negative bacteria has been guided by the need to have at least one positive charge present in the photosensitizer (3). Such photosensitizers are usually porphyrin derivatives (chlorins or bacteriochlorins) with molecular weights higher than 600 Da. Although photodynamic inactivation of bacteria suspensions by 5-6 orders of magnitude using micromolar photosensitizer concentrations and light doses ca. 10 J/cm$^2$ was achieved (4), the transfer to clinical applications has been unsuccessful. A likely reason for the failure to translate the photodynamic inactivation of bacteria suspensions to clinical settings is the incompatibility between the large size of the photosensitizers that absorb infrared light and the small molecular size required for rapid diffusion in the biofilms and uptake by the bacteria. Similar difficulties have been found in the transfer of PDT photosensitizers to the topical treatment of dermatological disorders. Whereas photosensitizers such as porfimer sodium (trade name Photofrin®) and temoporfin (Foscan®) have obtained approval for cancer indications using intravenous administration, topical applications have not been transferred to the clinical (5). Again, the failure of topical applications of photosensitizers to elicit therapeutic effects is likely related to the difficulty of such photosensitizers to cross the outer layer of the skin, called stratum corneum, and reach their targets. The stratum corneum is the principal barrier to the percutaneous penetration of exogenous molecules.

The best maximum flux ($J_{max}$) of a drug across the skin after topical application is strongly limited by the molecular weight (MW) of the drug (6), $$\log J_{max} = -3.90 - 0.0190 \text{ MW}$$

For example, drugs with MW=600 or 700 Da should have $J_{max}=5\times10^{-16}$ or $6\times10^{-18}$ mol/(cm$^2$ h), respectively. These calculations show that a modest increase in the molecular weight above 600 Da can lead to a dramatic decrease in the transdermal flux of the photosensitizers. In practical terms, a photosensitizer of 700 Da is likely to take 100 times longer to reach a therapeutic concentration in a subcutaneous target than a photosensitizer of 600 Da. Another critical property that drugs intended for topical applications must meet, is adequate solubility within the lipid domains of the stratum corneum to permit diffusion through this domain whilst still having sufficient hydrophilic nature to allow partitioning into the viable tissues of the epidermis. Drugs that meet this determinant have the logarithm of their n-octanol-water partition coefficient (log $P_{OW}$) between 1 and 3 (7).

The ideal photosensitizer for topical applications of PDT and for photoinactivation of bacteria must have a molecular weight MW<700 Da, a log $P_{OW}$ between 1 and 3, a high molar absorption coefficient $\varepsilon$>30,000 M$^{-1}$ cm$^{-1}$ between 650 and 850 nm, and a ROS quantum yield $\Phi_{ROS}$>0.3. Additionally, the photostability of the photosensitizer is also critical to the success of PDT (8). The photostability of a photosensitizer can be compared with the turnover of a chemical catalyst: it is related with the number of moles of substrate that a mole of catalyst can convert (i.e., the number of ROS generated) before the catalyst (i.e., photosensitizer) is inactivated (i.e., photodecomposes). The two most widely used photosensitizers for PDT of cancer are porfimer sodium (trade name Photofrin®) and temoporfin (proprietary name Foscan®). Porfimer sodium is a mixture of oligomers formed by ether and ester linkages of up to eight porphyrin units, relatively soluble in aqueous solutions, with log POW$\approx$0. Porfimer sodium is not a single molecular entity and does not have a characteristic molecular weight, but the molecular weight of the smallest dimmer exceeds 1000 Da. Temoporfin is the very lipophilic 5,10,15,20-tetra (m-hydroxyphenyl)chlorin with a molecular weight of 680 Da and log $P_{OW}$=5.5 at physiological pH. The singlet oxygen quantum yields of porfimer sodium and temoporfin are 0.36 and 0.43, respectively (8). Their maximum absorption peaks in the red are at $\lambda_{max}$=630 nm with a molar absorption coefficient $\varepsilon_{630}$=1170 M$^{-1}$ cm$^{-1}$ for porfimer sodium, and $\lambda_{max}$=650 nm with $\varepsilon_{650}$=29600 M$^{-1}$ cm$^{-1}$ for temoporfin. They are relatively photostable, with photodecomposition quantum yields $\Phi_{pd}$=5.5$\times$10$^{-5}$ and 3.3$\times$10$^{-5}$ for porfimer sodium and temoporfin, respectively. When porfimer sodium or temoporfin are incubated with CT26 (mouse colon adenocarcinoma) cells and, after washing, illuminated with laser light of the wavelength matching their red absorption bands to deliver a light dose of 1 J/cm$^2$, it was seen that a porfimer sodium concentration of 18 μM (estimated on the basis of the molecular weight of a porphyrin unit) was necessary to kill 50% of the cells in the culture (IC50=18 μM), whereas for temoporfin the concentration necessary to attain the same toxicity for the same light dose was 0.2 μM (IC50=0.2 μM) (8).

The properties of porfimer sodium are inadequate for the penetration of biological barriers, namely the skin, because of its exceedingly high molecular weight, hydrophilicity and modest light absorption in the phototherapeutic window. Temoporfin partially resolves the issue of the molecular weight but it is exceedingly lipophilic for transdermal delivery and absorbs light just at the limit of the phototherapeutic window. The difficulty of these clinically approved photosensitizers to permeate the biological barriers, namely the skin barrier, is aggravated by the need for relatively large concentrations of these photosensitizers in the biological target to attain the phototoxicity required for PDT to offer a good therapeutic outcome.

It has not been appreciated in earlier uses of photosensitizers for PDT that the ideal properties of a photosensitizer for PDT could be combined in a single molecule with the ideal properties of drugs for topical applications. The ability to rapidly diffuse through biological barriers is critical for the success of, for example, intradermal or transdermal delivery of photosensitizers topically applied in the treatment of dermatological disorders, penetration of the photosensitizers in biofilms for the photoinactivation of bacteria, diffusion of the photosensitizer through nails for the treatment of fungal infections such as onychomycosis. The ability to rapidly diffuse through biological barriers is also critical for the rapid accumulation of the photosensitizer in its biological target, such as the permeation through the outer membrane of eukaryote cells or the membrane of bacterial cells. Such rapid diffusions shorten the time between the administration of the photosensitizer and the illumination of the target, which is advantageous in many applications of photodynamic therapy, and increase the phototoxicity towards the target. It would not be expected by the person skilled in the art that the carboxamide group in at least one meso position of the halogenated porphyrin derivatives shown in formula (I), in particular bacteriochlorins and chlorins, could contribute to the amphiphilicity and photostability of such bacteriochlorin or chlorin derivatives without compromising the generation of ROS, and with such a small contribution to the molecular weight of the photosensitizer that its diffusion through biological barriers is not impaired.

This invention discloses for the first time photosensitizers for PDT of hyperproliferative disorders and/or for the photoinactivation of bacteria or virus or fungi that meet all the criteria for the ideal photosensitizer and efficiently permeate biological barriers. The present invention also discloses processes to synthesize such photosensitizers and, by the way of examples, illustrates the use of these photosensitizers to kill cancer cells and inactivate bacteria. In a further embodiment of the present invention, the photosensitizers described herein are used for the theranostics of hyperproliferative tissues. Theranostics is a modality of image-guided therapy where the same compound is used to visualize the biological target and to obtain the desired therapeutic effect.

SUMMARY OF THE INVENTION

The purpose of the present invention is to offer new carboxamide halogenated porphyrin derivatives, in particular bacteriochlorins and chlorins, which can be efficiently used to kill bacteria even when present in biofilms, to kill tumor cells even when applied topically, to kill fungi and to inactivate virus. In view of the shortcomings of the current PDT photosensitizers to achieve efficient transdermal delivery or to penetrate biofilms, the present invention discloses new porphyrin derivatives, in particular bacteriochlorins and chlorins, that combine low molecular weights, with strong absorption in the phototherapeutic window, high photostability, high quantum yields of ROS photogeneration, appropriate amphiphilicity and biocompatibility, and that can be produced in large quantities from inexpensive raw materials.

Another aim of the present invention is to offer a medication to be used in photodynamic therapy wherein the target is selected from the group consisting of: a vascular endothelial tissue, a neovasculature tissue, a neovasculature tissue present in the eye, an abnormal vascular wall of a tumor, a solid tumor, a tumor of the skin, a tumor of a head, a tumor of a neck, a tumor of an eye, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in the vascular system, a diseased bone marrow, and diseased cells in which the disease is one of an autoimmune and an inflammatory disease.

A further aim of the present invention is to offer a medication for the treatment of dermatological disorders such as psoriasis, acne vulgaris and rosacea; gynecological disorders such as dysfunctional uterine bleeding; urological disorders such as condyloma virus; cardiovascular disorders such as restenosis and atherosclerotic plaques; treatment of fungal infections such as onychomycosis; photodynamic destruction of bacteria or viruses, including multidrug-resistant bacteria; hair removal and cosmetics; inhibition of immune responses following the transplant of organs or tissues. The removal of a superficial layer of cells using the methods of photodynamic therapy with the photosensitizers disclosed herein stimulates the growth of new cells in the underlying skin layers with the subsequent improvement of skin appearance of cosmetic value. Another objective of the present invention is to provide a medication for heart arrhythmia consisting in the selective destruction of cells such as cardiac myocytes, by localized photodynamic therapy, and restoration of the physiological rhythm of the heart.

Finally, it is a further object of the invention to provide methods for the diagnosis of hyperproliferative tissues using new carboxamide porphyrin derivatives, in particular bacteriochlorins and chlorins. Provided that these compounds preferentially accumulate in such tissues, the additional property required for diagnostic purposes is the unambiguous detection of very minute quantities of such compounds. These compounds have very distinct absorption bands in the red and infrared, where the tissues are most transparent. The selective excitation of these compounds leads to distinct fluorescence at wavelengths where biological molecules do not emit. The detection of fluorescence can be made with very sensitive equipment and sub-nanomolar quantities of bacteriochlorins and chlorins can be measured in biological media. The source of irradiation for photodiagnosis and phototherapy is not restricted, but a laser beam is preferable because intensive light rays in a desired wavelength range can be selectively applied. It is necessary that the light rays have sufficient intensity to cause the compounds to emit fluorescence for diagnosis and to exert a cell killing effect for therapy. Additionally, when fluorinated chlorins or bacteriochlorins are employed, fluorine-MRI (Magnetic Resonance Imaging) can detect the accumulation of these compounds in small regions of the body and follow the metabolites formed in its clearance from the body. Moreover, when pulsed lasers are used for excitation, the subsequent radiationless decay processes release heat that generates a photoacoustic wave, and such waves can be detected by means of Photoacoustic Tomography providing further information of interest for the diagnosis of hyperproliferative disorders.

Other aims and technical features will appear in the following description that is given only by way of example and without being limited thereto.

The present invention relates to carboxamide porphyrin derivatives, in particular bacteriochlorin or chlorin, of formula:

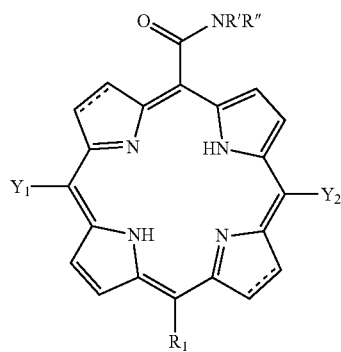

Formula (I)

Where:
═══ represents a carbon-carbon single bond or a carbon-carbon double bond, provided that at least one ═══ represents a carbon-carbon single bond;
$Y_1$, $Y_2$ are each independently chosen from hydrogen, halogenated alkyl or halogenated cycloalkyl with 6 or less carbon atoms, or halogenated phenyl where the halogens are independently chosen from F, Cl and Br, provided that at least one position of the alkyl, cycloalkyl or phenyl is halogenated, and provided that at least one of $Y_1$, $Y_2$ is not hydrogen i.e. at least one of $Y_1$, $Y_2$ is halogenated alkyl or halogenated cycloalkyl with 6 or less carbon atoms, or halogenated phenyl where the halogens are independently chosen from F, Cl and Br, provided that at least one position of the alkyl, cycloalkyl or phenyl is halogenated;
$R_1$ is chosen from H, I, Cl, Br or —CONR'R";
R' and R" are independently chosen from hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether or ester;
or pharmaceutically acceptable salts thereof.

Hence, the compounds of Formula (I) may be bacteriochlorins of formula

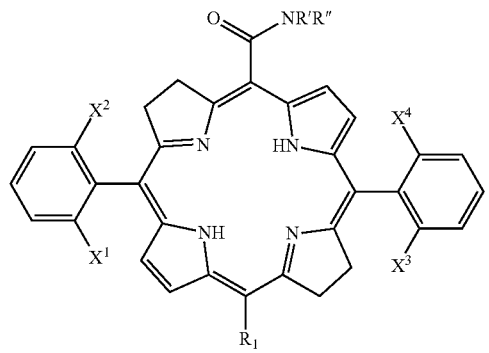

Formula (II)

Wherein:
$X^1$, $X^2$, $X^3$, $X^4$ are each independently chosen from halogen (F, Cl, Br) and hydrogen atoms, provided that at least $X^1$ and $X^3$ are halogens;
$R_1$ is chosen from H, F, Cl, Br or —CONR'R";
R' and R" are independently chosen from hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether or ester;
or pharmaceutically acceptable salts thereof.

Specific preferred compounds of the invention include the carboxamide bacteriochlorin of Formula (II) where $X^1$, $X^2$, $X^3$, $X^4$ are fluorine atoms, $R_1$ is hydrogen, R' is hydrogen and R" is methyl.

Alternatively, the compounds of Formula (I) may be chlorins of formula

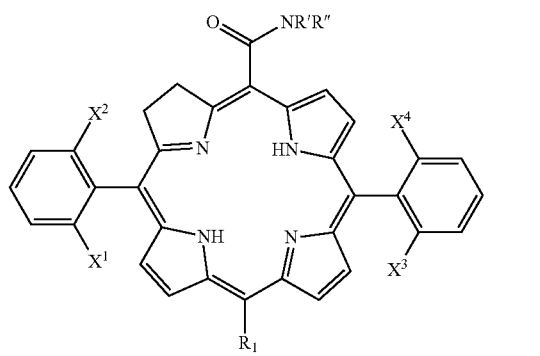

Formula (IIIa)

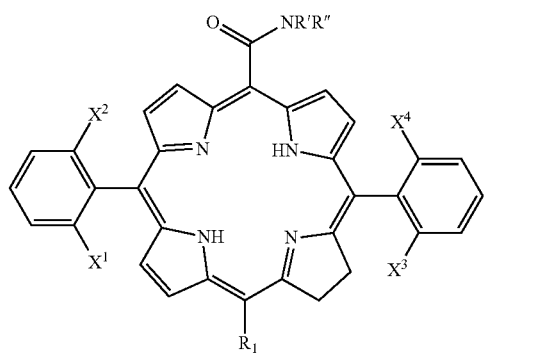

Formula (IIIb)

Wherein:
$X^1$, $X^2$, $X^3$, $X^4$ are each independently chosen from halogen (F, Cl, Br) and hydrogen atoms, provided that at least $X^1$ and $X^3$ are halogens;
$R_1$ is chosen from H, F, Cl, Br or —CONR'R";
R' and R" are independently chosen from hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether or ester;
or pharmaceutically acceptable salts thereof.

When $X^1$ is different from $X^2$ and/or $X^3$ is different from $X^4$, the compounds of Formula (II) or (III) have atropisomers because of the hindered rotation around the phenyl-macrocycle single bond. In such cases, the atropisomers can be distinguished by the number of heavier atoms on each side of the plane defined by the macrocycle. Formula IV illustrate two atropisomers of a bacteriochlorin derivative distinguished by the presence of both fluorine atoms on the same side of the macrocycle plane (atropisomer αα) or in different sides of the macrocycle plane (atropisomer αβ)

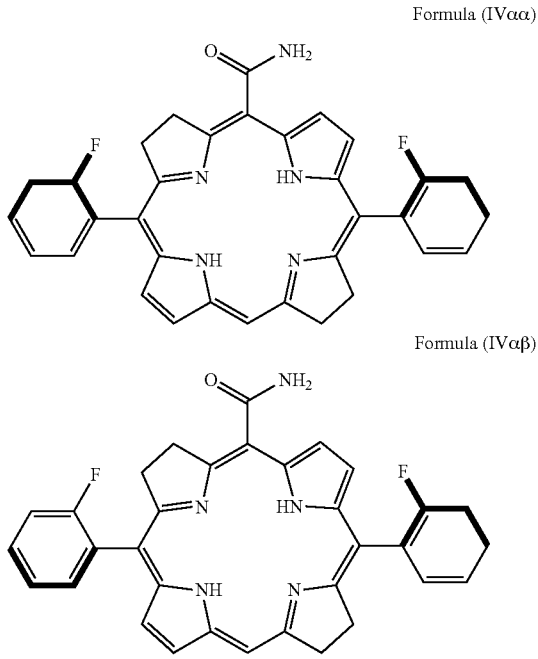

Formula (IVαα)

Formula (IVαβ)

Where the bold lines indicate that the bolded atoms, and the groups attached thereto, are sterically restricted so as to exist above the plane defined by the macrocycle ring.

The compounds of Formula (I) may also be bacteriochlorins of formula

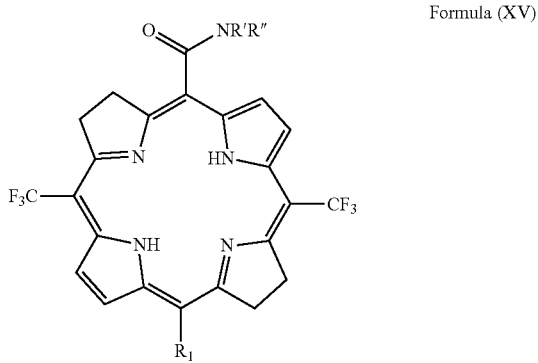

Formula (XV)

Wherein:

$R_1$ is chosen from H, I, Cl, Br or —CONR'R";

R' and R" are independently chosen from hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether or ester;

or pharmaceutically acceptable salts thereof.

Specific preferred compounds of the invention include the carboxamide bacteriochlorin of Formula (XV) where $R_1$ is hydrogen, R' is hydrogen and R" is methyl.

The invention also provides a pharmaceutical composition, comprising an effective amount a compound described herein and a pharmaceutically acceptable carrier.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient. In use, at least one compound according to the present invention is administered in a pharmaceutically effective amount to a subject in need thereof in a pharmaceutical carrier by intravenous, intramuscular, subcutaneous, intralesional, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect. Additionally, with photodynamic therapy, the "pharmaceutically effective amount" of the pharmaceutical composition or compound is partially dependent upon other factors such as light dose and oxygen, both of which are required to achieve a therapeutic result. Thus, there will also be an "effective amount" of light as well as amount of oxygen when treating a subject or patient. Other important factors that contribute to the determination of the "pharmaceutically effective amount" of drug, light, and oxygen include drug-to-light intervals (the time between drug administration and illuminating the tissue). Drug-to-light interval is important because, for example, administering a higher drug dose of 50 mg/kg and illuminating the tissue one week later with a light dose of 500 J/cm2 may be as inefficient or ineffective as using a drug dose of 0.01 mg/kg and illuminating the tissue 10 minutes after administration at a light dose of 0.1 J/cm2. The drug elimination (metabolism) by the organism between the administration of the drug and the illumination may decrease the effectiveness of the therapy when the drug-to-light interval increases (becomes longer). However, increasing the drug-to-light interval may lead to a more selective therapy and fewer adverse effectives. Thus, for at least these reasons, drug-to-light interval is an important factor to consider when determining the "pharmaceutically effective amount" of the compositions of the present invention.

In addition to the factors discussed above that affect the determination of the "effective amount" of drug, light, oxygen, and drug-to-light interval, a person of ordinary skill in the art would also take into account the fluence rate of the light (how many photons are delivered per unit area per unit time). Fluence rate is important because the delivery of too many photons too fast may deplete the oxygen in the tissue and render the therapy inefficient or ineffective.

A decided practical advantage of the present invention is that the compound may be administered in a convenient manner such as by intravenous, intramuscular, subcutaneous, oral, intralesional, or intracerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation or to improve dissolution.

The present invention also relates to a pharmaceutically composition comprising at least one of the derivatives complying with Formula (I), or pharmaceutically acceptable salts thereof, and a pharmaceutically acceptable carrier, which transiently permeabilizes the skin causing the pharmaceutical composition to be permeable through the various skin layers.

Another object of the present invention is the use of a compound as described herein in the manufacture of a medicament for use in the treatment of a disorder or disease described herein. Another object of the present invention is the use of a compound as described herein for use in the treatment of a disorder or disease described herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The present invention also relates to the use of the above mentioned derivatives or pharmaceutically acceptable salts thereof and the pharmaceutically composition comprising at least one of the same in the treatment of hyperproliferative disorders and/or cancer and/or bacterial and/or viral or fungi infections. Furthermore the use of the pharmaceutically composition in intradermal and transdermal therapies.

The present invention also relates to the use of the pharmaceutically composition comprising at least one of the above mentioned derivatives or pharmaceutically acceptable salts thereof in theranostics of hyperproliferative disorders, wherein at least one of the derivatives described in claims 1-9 associates with a target tissue is visualized by imaging technics and optionally through lighting said derivatives elicit the desired therapeutic effect in the target tissue. Where the imaging technics comprise Magnetic Resonance Imaging (MRI), exposing the derivatives complying with Formula (I), or pharmaceutically acceptable salts thereof, to light of sufficient energy to cause the same to fluoresce, or comprise exposing the derivatives complying with Formula (I), or pharmaceutically acceptable salts thereof, to a light pulse of picosecond or nanosecond duration, of sufficient energy to cause the compound to launch a photoacoustic wave.

Remarkably, the molecular weight of bacteriochlorins or chlorins of Formula (I) range between 425 Da and 700 Da, they are amphiphilic, form few hydrogen bonds and may diffuse efficiently through biological barriers such as the stratum corneum or through biofilms. One of the technical characteristics of these derivatives lies in their low molecular weight and the consequent increased flux through protective biological barriers. Another technical advantage is the preservation of the bacteriochlorin, or chlorin, macrocycle known for its strong absorption of light in the phototherapeutic window and ability to generate ROS in high quantum yields. Yet another advantage is the presence of substituent groups that enhance the photostability of reduced porphyrin derivatives and balance the solubility within lipid domains with biocompatibility with biological and pharmaceutical carriers. A further technical characteristic of the bacteriochlorins or chlorins with Formula (I) is that they are significantly fluorescent, namely with fluorescence quantum yields higher than 0.1, which allows for their non-invasive visualization in the target. This visualization is a desired property because it enables the visualization of the target and the choice of the best timing to start the therapy, for instance when the photosensitizer target-to-surrounding tissue ratio is high. The theranostic use of bacteriochlorins or chlorins with Formula (I) can also be exploited when they contain fluorine atoms, by means of fluorine magnetic resonance imaging (MRI), or when they launch photoacoustic waves under pulsed laser light, by means of photoacoustic tomography (PAT).

Herein, the meaning of "protective biological barriers" should be understood as barriers to the diffusion of molecular and supramolecular species in the body, such as the skin and more particularly the stratum corneum, barriers of the gastrointestinal tract and also ocular barriers, the nail barrier, the outer membrane of cells and bacteria, and also the biofilms created by microorganisms. It could not be anticipated by the person skilled in the art that carboxamide halogenated porphyrin derivatives, in particular bacteriochlorins and chlorins, could efficiently permeate biological membranes and rapidly become very phototoxic photosensitizers towards malignant cells, bacteria or fungi protected by said biological barriers.

BRIEF DESCRIPTION OF THE DRAWINGS

Without intent to limit the disclosure herein, this application presents attached drawings of illustrated embodiments for an easier understanding.

DESCRIPTION OF THE EMBODIMENTS

Figure 1:
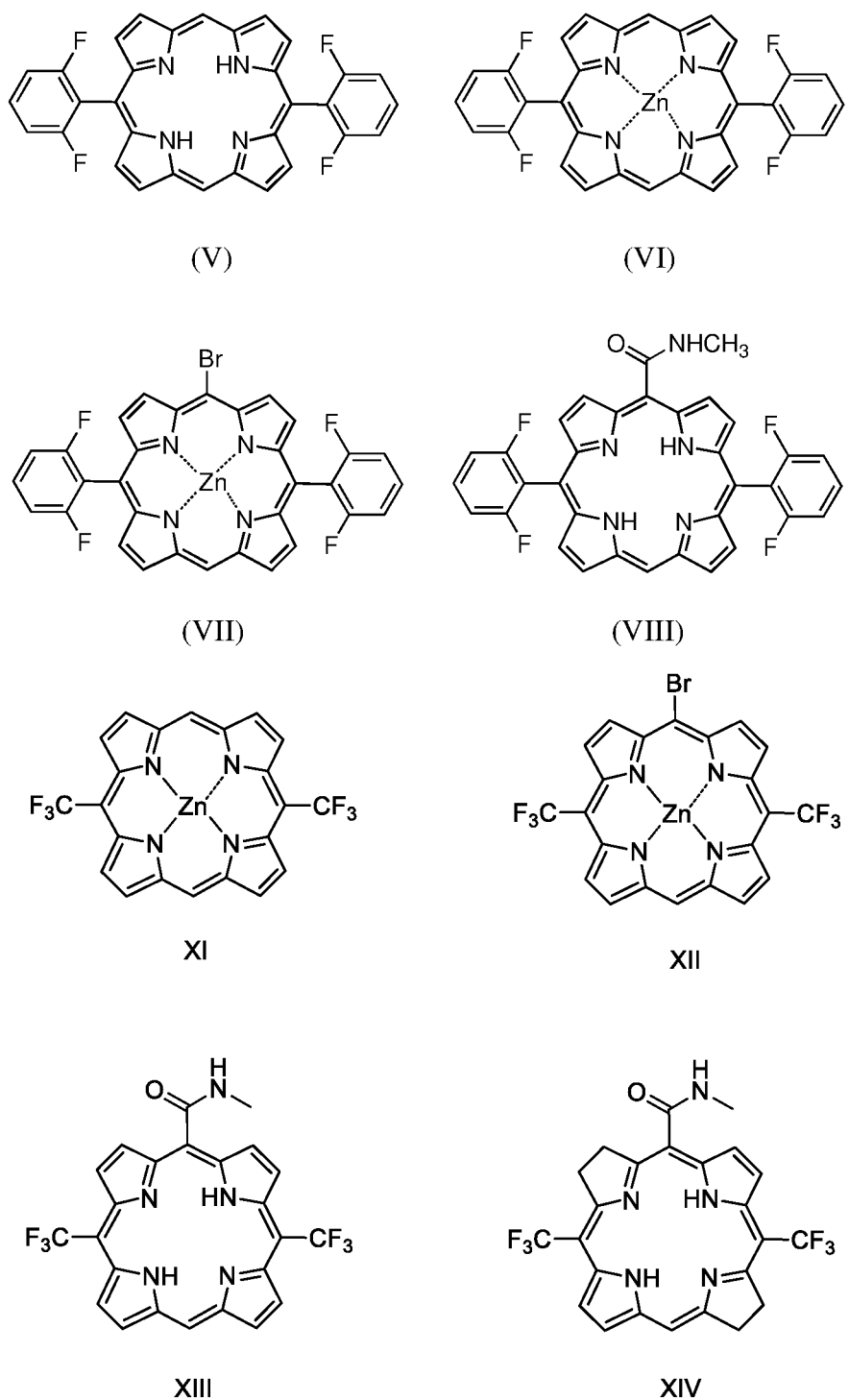
FIG. 1: A) Structures of the molecules of formula (V), (VI), (VII), and (VIII). B) Structures of the molecules of formula (XI), (XII), (XIII), and (XIV).

Referring to the drawings, herein are described optional embodiments in more detail, which however are not intended to limit the scope of the present application.

A. Precursor Compounds

A.1. 5,15-bis-(2,6-Difluorophenyl)porphyrin precursors 5,15-bis-(2,6-Difluorophenyl)porphyrin (Formula V in FIG. 1) was prepared with a modification of a method for the preparation of 5,15-diphenylporphyrins (9a). The equimolar mixture of commercially available 2,2'-dipyrromethane and 2,6-difluorobenzaldehyde was allowed to react in the presence of trifluoroacetic acid (TFA). After oxidation with 2,3-dichloro-5,6-dicyano-1,4-benzoquinone (DDQ), workup and purification, V was obtained with 35% yield in a multigram gram scale (~5 g). The characterization of V is as follows: $^1$H NMR: (400 MHz, (CDCl$_3$) δ ppm: −3.05 (s, 2H, —NH); 7.55-7.79 (t, 4H, Ar—H); 7.98-8.05 (m, 2H, Ar—H); 9.03 (d, J=4.4 Hz, 4H, β-H); 9.41 (d, J=4.5 Hz, 4H, β-H); 10.32 (s, 2H, meso-H); MS (ESI-FIA-TOF): m/z calcd for (C$_{32}$H$_{19}$F$_4$N$_4$) [M+H]$^+$ 535.1540; found: 535.1536 [M+H]$^+$.

[5,15-bis-(2,6-Difluorophenyl)porphyrinato] zinc (II) (Formula VI) was prepared by the complexation of 5,15-bis(2,6-difluorophenyl)porphyrin with zinc acetate (Zn(OAc)$_2$) in a mixture of dichlomethane:methanol 1:1. The solution was heated up with magnetic stirring until the starting material was fully consumed. The solution was washed with water, dried with anhydrous sodium sulfate, filtered, and concentrated via rotary evaporation; 4.3 g of isolated product was obtained with 99% yield. The NMR of the isolated product is as follows: $^1$H NMR: (400 MHz, (CDCl$_3$) δ ppm: 7.41-7.45 (t, 4H, Ar—H); 7.81-7.86 (m, 2H, Ar—H); 9.13 (d, J=4.3 Hz, 4H, β-H); 9.50 (d, J=4.5 Hz, 4H, β-H); 10.37 (s, 2H, meso-H).

[5-bromo-10,20-bis-(2,6-difluorophenyl)porphyrinato] zinc (II) (Formula VII) was synthesized by the reaction of N-bromosuccinimide (NBS) (298 mg±10 mg) dissolved in dichloromethane (DCM) (100±20 mL) added drop wise to a mixture of 1 g of [5,15-bis-(2,6-difluorophenyl)porphyrinato]zinc (II) in DCM (400±50 mL) and pyridine (1.35±0.5 mL) at −6° C. After 1 h the reaction is completed, water was added (50±20 mL) and the organic layer was sequentially washed with a solution of hydrochloric acid 0.1 M (3 times) and water (3 times). The solvent was evaporated and purified by column chromatography with silica gel (DCM/hexane). The [5-bromo-10,20-bis-(2,6-difluorophenyl)porphyrinato] zinc (II) was obtained with 70±5% yield (790±40 mg). $^1$H NMR: (400 MHz, (CDCl$_3$) δ ppm: 7.34-7.38 (m, 4H, Ar—H); 7.76-7.79 (m, 2H, Ar—H); 8.83 (s, 4H, β-H); 9.26 (d, J=4.5 Hz, 2H, β-H); 9.70 (d, J=4.7 Hz, 2H, β-H); 10.13 (s, 1H, meso-H).

5-Methylamide-10,20-bis-(2,6-difluorophenyl)porphyrin (Formula VIII) was synthesized via aminocarbonylation reaction. An autoclave steel reactor containing a stirring bar, was charged with 4.0 g (5.9 mmol) of [5-bromo-10,20-bis(2,6-difluorophenyl)porphyrinato] zinc(II), 66.0 mg (0.3 mmol) of palladium acetate (Pd(OAc)$_2$), 155.0 mg (0.6 mmol) of triphenylphosphine, 0.8 mL (5.9 mmol) of trimethylamine, 14.6 mL (29.5 mmol) of 2 M methylamine solution in tetrahydrofuran (THF), and 60.0 mL of dry THF. The reactor was closed and charged with 5 bar of carbon monoxide. The mixture was stirred at 70° C. and the reaction was allowed to proceed for 15 hours. The reaction mixture was transferred to a round bottom flask and the solvent removed in the rotatory evaporator. The reaction crude was dissolved in DCM and TFA (10 ml) was added. The reaction mixture was stirred at room temperature for 2 hours. The work-up was performed by a liquid-liquid extraction using a saturated sodium bicarbonate solution and distilled water. The organic layer was dried with anhydrous sodium sulfate, filtered and finally the solvent was removed in a rotary evaporator. After column chromatography (silica gel, DCM: ethyl acetate, 20:1) 2.45 g of isolated product was obtained with 70% yield. The NMR and MS of the isolated product are as follows: $^1$H NMR: (400 MHz, (CD$_3$)$_2$CO) δ ppm: −3.14 (s, 2H, —NH); 3.56 (d, J=4.2 Hz, 3H, —CH$_3$); 7.63 (t, J=8.2 Hz, 4H, Ar—H); 8.04-8.11 (m, 2H, Ar—H); 8.49 (bs, 1H, —NH); 9.09 (m, 4H, β-H); 9.63 (d, 2H, J=4.5 Hz, β-H), 9.56 (d, 2H, J=4.7 Hz, β-H); 10.60 (s, 1H, meso-H). MS (ESI-FIA-TOF): m/z calcd for C$_{34}$H$_{22}$F$_4$N$_5$O: 592.1760; found: 592.1751 [M+H]$^+$.

A2. 5,15-bis-(Trifluoromethyl)porphyrin precursors

[5,15-bis-(Trifluoromethyl)porphyrinato]zinc(II) (Formula XI in FIG. 1) was synthesized using a previously described method (9b). The characterization of XI is as follows: $^1$H RMN: (400 MHz, THF-ds) δ ppm: 9.67 (d, J=4.0, β-H); 9.88 (bs, β-H); 10.57 (s, 2H, meso-H). [5-Bromo-10,20-bis-(trifluoromethyl)porphyrinato]zinc(II) (Formula XII) was synthesized by the reaction of N-bromosuccinimide (NBS) dissolved in dichloromethane, added drop wise to a mixture of [5,15-bis-(trifluoromethyl)porphyrinato]zinc(II) in dichloromethane and pyridine at −6° C. After 1 h, the reaction is complete. Water was added and the organic layer was sequentially washed with a solution of hydrochloric acid 0.1 M (3 times) and water (3 times). The solvent was evaporated to dryness and the compound was used in the next reaction step.

5-Methylamide-10,20-bis-(trifluoromethyl)porphyrin (Formula XIII) was synthesized via aminocarbonylation reaction. An autoclave steel reactor containing a stirring bar, was charged with [5-bromo-10,20-bis-(trifluoromethyl)porphyrinato]zinc(II), palladium acetate, triphenylphosphine, triethylamine, methylamine and dried THF. The reactor was closed and charged with a pressure up to 10 bar of carbon monoxide. The mixture was stirred at 70° C. and the reaction was allowed to proceed for 15 hours. The reaction mixture was transferred to a round bottom flask and the solvent removed in the rotatory evaporator. The reaction crude was dissolved in dichloromethane and trifluoroacetic acid was added. The reaction mixture was allowed to stir at room temperature during 2 hours. The work-up was performed by a liquid-liquid extraction using a saturated sodium bicarbonate solution and distilled water. The organic layer was dried with anhydrous sodium sulfate, filtered and finally the solvent was removed in rotary evaporator. After column chromatography (silica gel, dichloromethane:hexane) the product was isolated. The characterization of XIII is as follows: $^1$H RMN: (400 MHz, THF-d$_8$) δ ppm: −2.84 (s, 2H, —NH); 3.56 (d, J=4.2 Hz, 3H, —CH$_3$); 8.72 (bs, 1H, —NH); 9.66-9.68 (m, 4H, β-H); 9.80 (bs, 4H, β-H); 10.62 (s, 1H, meso-H).

B. Materials and Methods

Elemental analyses were carried out on a Leco TruSpec CHNS elemental analyzer. $^1$H-NMR and $^{19}$F-NMR and spectra were recorded on a Bruker Avance 400 MHz. 1H assignments were made using 2D COSY and NOESY experiments, ESI-FIA TOF High Resolution Mass Spectrometry data were acquired using a Micromass Autospec mass spectrometer. HPLC Shimadzu Prominence equipped with a Diode Array (model SPD 20 AV). Separations were followed at 743 nm, 23° C. on a semi-preparative column Inertsil-Phenyl (250*10 mm; 5 μm).

Optical Absorption:

The UV-Vis-NIR optical absorption was recorded with an Agilent Cary5000 UV-Vis-NIR Spectrophotometer in the determination of the molar absorption coefficient and with Shimadzu UV-2100 spectrometer in routine measurements. The absorption spectra were recorded in the wavelengths from 300 nm up to 800 nm.

Fluorescence Emission:

The fluorescence emission spectra were recorded in the homemade setup composed of a Horiba-Jobin Fluoromax 4, used to excite the samples, connected to a sample holder through an optical fiber. In the sample holder, perpendicular to excitation fiber, an optical fiber is connected to drive the emission light to the spectrophotometer detector Avantes model SensLine, provided with AvaSoft 7.7.2. The excitation slit was set at 2 mm and the integration time was 3 s, with average number of 3. The spectra were collected from 200 nm up to 1100 nm using standard cuvettes of 1 cm of optical path. Fluorescence quantum yields ($\Phi_F$) were obtained comparing the integrated fluorescence of the samples with that of a reference fluorimetric compound with known $\Phi_F$.

Fluorescence Lifetime:

The fluorescence lifetime was determined in homemade equipment composed of a LED that produces a light pulse for exciting the sample, a sample holder, detector and optics. The excitation wavelength was set at 373 nm and the emission collected at 737 nm. The signal was collected using 1024 channels with temporal scale of 28.5 ps per channel.

Transient Absorption:

The triplet-triplet transient absorption was recorded in an Applied Photophysics LKS.60 laser flash photolysis spectrometer, with a Hewlett-Packard Infinium Oscilloscope and a Spectra-Physics Quanta-Ray GCR-130 Nd:YAG laser as excitation source. The pulse excitation was set at 355 nm.

Singlet Oxygen Quantum Yield:

The experiments were run at room temperature using the Nd-YAG laser Spectra-Physics Quanta-Ray GRC-130. The solutions were excited at 355 nm and the phosphorescence of singlet oxygen collected at 1270 nm in a Hamamatsu R5509-42 photomultiplier, cooled to 193 K in a liquid nitrogen chamber, after selection of the wavelength with a monochromator with 600 lines grading. Phenalenone was used as a reference of singlet oxygen generator. A Newport filter model 10LWF-1000-B was used in the emission to avoid scattering and fluorescence.

Photoacoustic Calorimetry:

The thermal energy released after electronic excitation was measured by time-resolved photoacoustic calorimetry using a front-face irradiation photoacoustic cell and a EKSPLA OPO model PG-122 pumped by an EKSPLA Nd:YAG. The signal detection was made using a 2.25 MHz Panametrics transducer. The excitation was at 690 nm and azulene was used as photoacoustic calorimetry reference.

n-Octanol:PBS Partition Ratio:

a modification of the shake-flask method was employed to determine the equilibrium concentrations of the photosensitizer in n-octanol and in phosphate-buffered saline (PBS) mixed in equal volumes, using the typical fluorescence band of the same photosensitizer and calibration curves.

Photobleaching experiments were conducted in methanol:PBS (3:2) and in organic solvents. The solutions were irradiated in a cuvette with an optical path of 1 cm using a CW laser emitting at 749±3 nm from Omicron Laserage. The total output power was 212 mW or 244 mW. For each compound, the absorbance was collected in time intervals from few minutes up to hours of irradiation.

Phototoxicity towards bacteria was evaluated in vitro against *P. acnes* (ATCC® 6919—Remel, Lenexa, Kans., USA) using light with the appropriate wavelength. *P. acnes* bacteria was cultured in Reinforced Clostridial Medium (Oxoid, Basingstok, UK) under anaerobic atmosphere at 37° C. Anaerobic growth conditions were obtained using an anaerobic jar with a sachet for anaerobic conditions generation (Anaerocult A, Merck, Darmstadt, Germany). *P. acnes* suspension was diluted with culture medium to an optical density at 620 nm of 1.3, corresponding to approximately 1×10 CFU/ml (colony-forming units per milliliter). The diluted suspension was centrifuged at 13000 rpm for 10 minutes, and re-suspended in PBS. Test compound stock solutions were dissolved in PEG400:DMSO (propylene glycol 400:dimethyl sulfoxide) (55:45) and were diluted to the appropriate concentrations with PBS. The incubation of the test compounds with *P. acnes* was performed in DB Falcon black 96-well plates with clear flat-bottom (Franklin Lakes, N.J., USA), in the absence of light, during 30 minutes. After the incubation period, the plates were irradiated with a LED light from Marubeni (model L740-66-60-550), emission maximum at 740 nm with FWHM=25 nm, appropriate to excite bacteriochorins, for a total light dose of 4 or 10 J/cm². After the irradiation the contents of each well were centrifuged at 13000 rpm for 10 minutes and re-suspended in culture medium. The plate with *P. acnes* was incubated at 37° C. for 24 h, under anaerobic atmosphere. After the incubation period, the viability of *P. acnes* was evaluated. The bacterial suspensions in the plate wells were diluted with culture medium and seeded in Petri dishes with Reinforced Clostridial Agar (Oxoid, Basingstok, UK) for later count of CFU. The petri dishes were incubated at 37° C. for at least 72 h, under anaerobic atmosphere.

Phototoxicity towards cancer cell lines was evaluated in vitro using A549 (human lung adenocarcinoma) and CT26 (mouse colon adenocarcinoma) cell lines. The cells were cultured in Dulbecco's modified Eagles's medium (DMEM) supplemented with 10% heat-inactivated fetal bovine serum and 1% penicillin. Cells were plated at a density of 20,000/well and 15,000/well respectively, in flat-bottom 96-well plates. On the following day, diluted solutions of the test compound were prepared (1 mM stock) and added to the cells for 30-min incubation. PEG400:DMSO (55:45) concentration in the medium did not exceed 1%. The wells were washed two times with PBS and irradiated after 30-min of incubation using the LED light described above. Light dose was 1 J/cm². The medium was replaced with fresh one after irradiation and the plates were incubated for 24 h, at which time the cellular viability was assessed by resazurin method using a microplate spectrophotometer (Synergy HT Biotek).

Photodynamic therapy of female BALB/c mice bearing tumors was approved by the National Veterinary Authority (DGVA authorization no. 0420/000/000/2011). Mice weighing 18-20 g (Charles River Laboratories, Barcelona, Spain)

were kept on a standard laboratory diet with free access to drinking water. The tumor model was established taking up 350.000 CT26 cells (CRL-2638™, ATCC-LCG Standards, Barcelona, Spain) in 0.1 ml PBS and inoculated the cells subcutaneously in the right thigh of each mouse. The light source used for PDT in vivo was a custom-made diode laser, model LDM750.300.CWA.L.M with controller 1201-08P and laser head 1201-08D (Omicron, Rodgau, Germany), coupled to an optic fiber with a fixed divergent lens, model FD with a diameter of 2 mm (Medlight, Ecublens, Switzerland).

Skin permeation was evaluated using a topical formulation containing benzyl alcohol (23%), Kolliphor EL (17%), Transcutol (50%) and water (10%). The photosensitizer added to this formulation corresponded to 1.85% of the mass before its addition, and the gelling agent (Aerosil 200) added corresponded to 5% of the mass before its addition. The photosensitizer was first dissolved in Transcutol and exposed to 3 min of vortex and 5 min of ultrasounds. A mixture of benzyl alcohol and Kolliphor EL was then added. Immediately after, it was mixed in an IKA MIXER at 200 rpm for 5 min and water was added drop-by-drop for 10 min. Finally, the gelling agent, Aerosil 200, was mixed in and the microemulsion gel was obtained. Skin permeation studies were performed in pig skin using samples collected from 5 months old pigs. The hair was removed as well as the underlying fatty layer, before the permeation studies.

C. Properties of the Compounds

The absorptivities of the compounds were measured at several concentrations, in the μM range, and in all cases were observed to follow the Beer-Lambert law. Additionally, the wavelength of maximum absorption ($\lambda_{max}$) in the infrared did not vary in the concentration range studied. This is indicative of negligible aggregation between the molecules, which exist mostly as monomers at these concentrations in the solvents studied. Table 1 presents the infrared molar absorption coefficient ($\varepsilon_{max}$) and wavelength maximum in ethanol of a typical carboxamide halogenated bacteriochlorin derivative of Formula (I). The same table also presents triplet lifetimes ($\tau_T$) in air and $N_2$ saturated solutions, fluorescence lifetime ($\tau_S$), the quantum yields of fluorescence ($\Phi_F$), triplet state formation ($\Phi_T$), and singlet oxygen generation ($\Phi_\Delta$) in ethanol, and photodegradation quantum yield ($\Phi_{pd}$) in methanol:PBS (3:2). Triplet decays were clearly mono-exponential and in air-saturated ethanol the triplet lifetimes were in the range of 200 to 300 nanoseconds. Such values are consistent with diffusion limited energy transfer from the triplet state of the photosensitizer to molecular oxygen through a charge-transfer interaction (8). The absorption intensity of the test compounds in the photobleaching studies followed a mono-exponential decrease as a function of the illumination time.

The typical photophysical, photochemical and photobiological properties of carboxamide porphyrin derivatives, in particular bacteriochlorins or chlorins, of formula (I) remedy the shortcoming aforementioned of current photosensitizers employed in PDT. In particular, the molecules of Formula (I) can have low molecular weights and may attain high fluxes through biological membranes. The incubation times employed to obtain the phototoxicities illustrated in Table 1 were 30 minutes only, whereas incubation times of 18 h were used to obtain the IC50 values of porfimer sodium and temoporfin discussed above. Moreover the IC50 value of bacteriochlorins or chlorins of formula (I) can be several orders of magnitude lower than those of porfimer sodium or temoporfin, which means that the bacteriochlorins or chlorins of formula (I) attain the same phototoxicity as the clinically approved photosensitizers at orders of magnitude lower concentrations. This will allow such photosensitizers to reach the concentration required to elicit a therapeutic effect within a short period of contact with the protective biological barrier. Moreover, the carboxamide group introduces adequate amphiphilicity for biocompatibility and crossing of biological barriers, namely leading to values of log $P_{OW}$ between 1 and 3. This substituent, together with the halogen atoms in the substituents in the meso positions also contributes to enhance the photostability of porphyrin derivatives of Formula (I), which is comparable to that of clinically approved photosensitizers.

The conjugation of photostability, strong absorption in the phototherapeutic window, high yield of ROS and amphiphilicity offers another advantageous technical characteristic to the porphyrin derivatives of formula (I): very high phototoxicity towards bacteria and cancer cells. Table 1 shows an example of a photosensitizer according to Formula (I) that incubated in a 2 μM concentration with $P.$ $acnes$ colonies and illuminated with 10 $J/cm^2$ of light absorbed by its red absorption band reduces by 9 orders of magnitude the number of bacterial CFU. The phototoxicity against tumor cells is equally impressive. The photosensitizer drug doses that kill more than 50% of a population of cancer cells in vitro (IC50) under a light dose of 1 $J/cm^2$ are below 10 nM.

The ability of porphyrin derivatives, in particular bacteriochlorin or chlorin, of Formula (I) to cross protective biological barriers and diffuse rapidly to they target, combined with their high phototoxicity when illuminated with light in the phototherapeutic window, make these bacteriochlorins or chlorins especially suitable for anti-cancerous and/or antimicrobial and/or antiviral and/or anti-fungi medications for human or animal usage exhibiting as a main active agent one or several porphyrin derivatives described in the present invention. This type of medication, used in particular in PDT, may also contain one or several pharma-

TABLE 1

Photophysical and photochemical properties of the carboxamide bacteriochlorin of formula IX in ethanol and photodecomposition quantum yield in methanol:PBS (3:2), together with photobiological properties in bacteria ($P.$ $acnes$ incubated with 2 μM and irradiated with 10 $J/cm^2$) and in cancer cell (A549 and CT26 irradiated with 1 $J/cm^2$) cultures.

| λ | ε (λ)/ $10^3$ | $\tau_S$ | $\Phi_F$ | $\tau_T$ (air) | $\tau_T$ ($N_2$) | $\Phi_\Delta$ | $\Phi_T$ | $\Phi_{pd}$/ $10^{-4}$ | Log $P_{OW}$ | log CFU P. Acnes | IC50/nM A549 | IC50/nM CT26 |
|---|---|---|---|---|---|---|---|---|---|---|---|---|
| nm | $M^{-1}$ $cm^{-1}$ | ns | | ns | μs | | | | | | | |
| 734 | 69 | 3.2 | 0.20 | 210 | 71 ± 5 | 0.38 | 0.45 | 1.5 | 2.9 | 9 | 2.5 | 5.8 | ceutically acceptable excipients. In PDT a pharmaceutical formulation containing one or several of the compounds described in the present invention is administered either topically, orally or systemically to the subject, and after some time (the drug-to-light interval), the target tissue is illuminated with light absorbed by porphyrin derivatives, preferably bacteriochlorins or chlorins. The percentage of photosensitizer present in the topical formulation may vary from 0.01% to 15%. The dose of light used to activate the photosensitizer applied topically may also vary, and doses between 1 and 100 J/cm$^2$ may be required. These light doses may be delivered with light sources that match the absorption band of the photosensitizer in the phototherapeutic window, provided that these light sources have irradiances below the onset of thermal effects, which is close to 250 mW/cm$^2$. Alternatively, the light doses can be given over a long period of time, including making use of solar exposure of the areas where the topical formulation was applied. The systemic administration of photosensitizers used in PDT is made using pharmaceutically acceptable carriers, to obtain photosensitizer doses ranging from 0.1 to 10 micromole/kg body mass. After a drug-to-light interval that may range from concomitant with the drug administration to 5 days after the administration, the light dose is delivered to the target. The reactive oxygen species generated by the illuminated photosensitizer molecules trigger a cascade of chemical and biological processes that culminate in the death of the cells and/or bacteria and/or virus.

The compounds of the present invention may also fluoresce with high quantum yields and in the phototherapeutic window. Table 1 presents an example of a photosensitizer with $\Phi_F$=0.20. This typical fluorescence can be used to detect the presence of the compound in the target tissue and offers the possibility of using the compounds of the present invention for the diagnosis of vascular or hyperproliferative disorders.

The compounds of the present invention also loose energy through radiationless processes with high quantum yields. Table 1 presents an example of a photosensitizer with ($\Phi_F$=0.20 and $\Phi_T$=0.45 that must have an internal conversion quantum yield of $\Phi_{ic}$=0.35. The thermal energy lost in the 3.2 ns lifetime of the singlet state produces a fast thermoelastic expansion that launches an intense photoacoustic wave. Ultrasonic transducers can be used to detect photoacoustic waves, as described above for photoacoustic calorimetry. Alternatively, they can be detected by means of Photoacoustic Tomography and be used in the diagnosis of vascular or hyperproliferative disorders.

D. Description of Methods of Preparation of the Compounds

Another aim of the present invention consists in the method of preparation of the derivatives described above.

Non-symmetric 5,15-disubstituted porphyrins were prepared with a modification of the method of condensation-cyclization of commercially available 2,2'-dipyrromethane with halogenated aldehydes using TFA as catalyst in DCM under inert atmosphere (10), followed by a step of oxidation of the porphyrinogen to the corresponding porphyrin with DDQ as oxidant. The next steps encompass the metalation of 5,15-disubstituted porphyrins with zinc acetate in DCM/methanol (1:1) solution (11), followed by mono or di-halogenation of 10 or 10,20-porphyrinic positions. The porphyrinate zinc(II) complex was brominated with NBS, chlorinated with N-chlorosuccinimide (NCS), iodinated with bis(trifluoroacetoxy)iodobenzene or 2,6-dichloro-1-fluoropyridinium triflate (9a). Although the aminocarbonylation reaction is a standard process for the preparation of carboxamides from aryl halides or aryl triflates and amines, the aminocarbonylation of porphyrins is uncommon (12). Carboxamide porphyrins were prepared by aminocarbonylation of the corresponding halogenated precursors, preferentially the brominated one, with methylamine at low pressures of carbon monoxide (1-10 bar) and temperature between 50-100° C., in the presence of a base, and using a transition metal complex ($ML_n$) catalyst. The metal can be chosen from molybdenum, chromium, nickel or, preferentially, palladium. The ligands in the transition metal complex can be chosen from 1,2-bis(diphenylphosphino)ethane (DPPE), 4,5-bis(diphenylphosphino)-9,9-dimethylxanthene (Xantphos), 1,2-bis(diphenylphosphino)propane (DPPP) 1,2-bis(diphenylphosphino)butane (DPPB), 2,2'-bis(diphenylphosphino)-1,1'-binaphthyl (BINAP), bis-[2-(diphenylphosphino)phenyl] ether (DPEPhos), 2-di-tert-butylphosphino-2',4',6'-triisopropylbiphenyl (t-BuXpho), tri-n-alkylphosphine or, preferentially, triphenylphosphine ($PPh_3$). The base can be inorganic and selected from carbonates, phosphates or fluorinates. The base can also be organic and selected from amines, preferentially triethylamine. The solvent can be selected from toluene, dioxane, N-methyl-2-pyrrolidone (NMP), dimethylformamide (DMF), DCM or THF. Alternative sources of CO may also be employed, namely ($M(CO)_n$) where M is Mo or Co. Schematically, the preparation of the porphyrin precursors may be described as follows

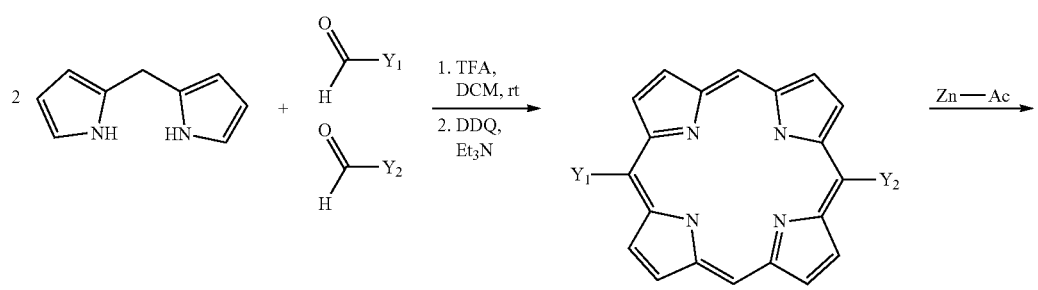

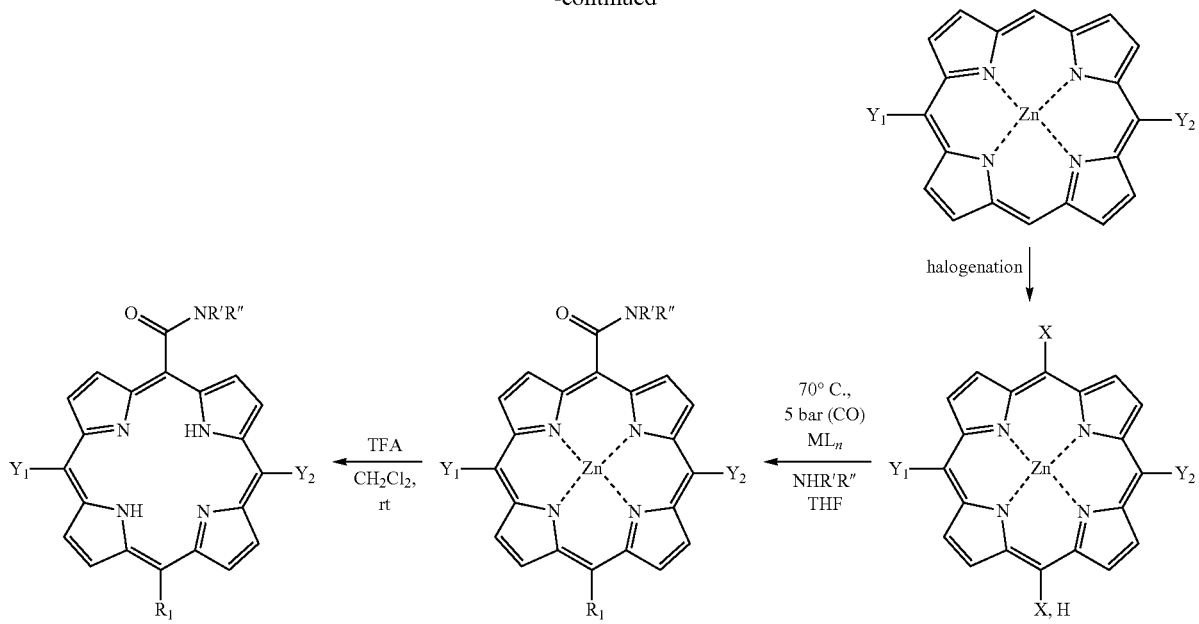

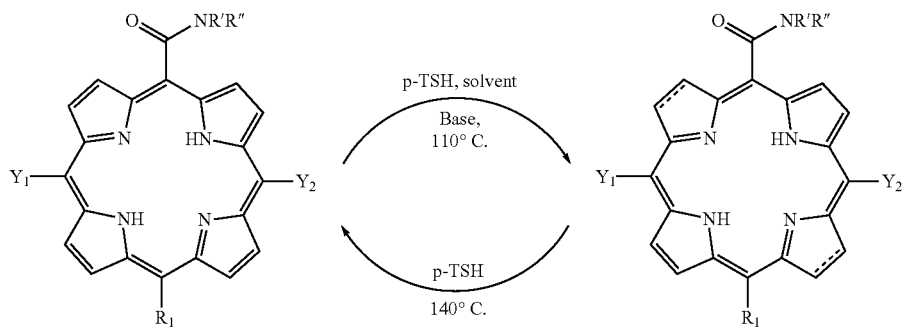

Wherein:

$Y_1$, $Y_2$ are each independently chosen from hydrogen, halogenated alkyl or halogenated cycloalkyl with 6 or less carbon atoms, or halogenated phenyl where the halogens are independently chosen from F, Cl and Br, provided that at least one position of the alkyl, cycloalkyl or phenyl is halogenated, and provided that at least one of $Y_1$, $Y_2$ is not hydrogen;

$R_1$ is chosen from H, F, Cl, Br or —CONR'R";

R' and R" are independently chosen from hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether or ester.

The carboxamide halogenated porphyrin precursors are then used to obtain the corresponding reduced bacteriochlorins or chlorins. The reduction was based on the diimide reduction method using hydrazide as the hydrogen source, preferably using p-toluenesulfonyl hydrazide (p-TSH), inorganic or hindered organic bases, in solvents selected from DMF, toluene, xylene, pyridine and picoline, using a modification of the method disclosed in PCT/EP2005/012212. The reduction can also take place in the absence of solvents and in the absence of bases, using a modification of the method disclosed in PCT/PT2009/000057. The reduction of the carboxamide porphyrin to the corresponding bacteriochlorin or chlorin may be described as follows:

Where: ═══ represents a carbon-carbon single bond or a carbon-carbon double bond, provided that at least one ═══ represents a carbon-carbon single bond.

EXAMPLES

Figure 2:
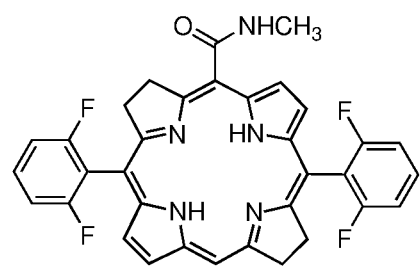
FIG. 2: Structures of the molecules of formula (IX), (Xa), and (Xb).
Figure 2:
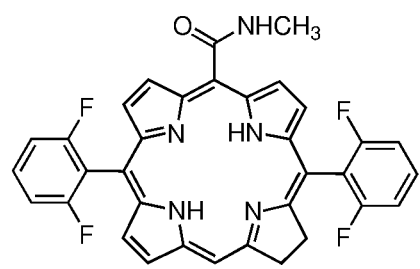
Figure 2:
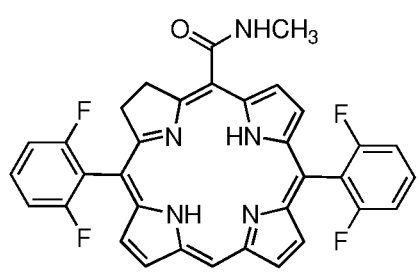

This invention will now be described in more detail in the following non-limiting EXAMPLES, with reference to the following drawings:

Example 1. Procedure for the Preparation of 5-methylcarboxamide-10,20-bis-(2,6-difluorophenyl)chlorin The synthesis of 5-methylcarboxamide-10,20-bis-(2,6-difluorophenyl)chlorin was performed by the reaction of p-toluenesulphonyl hydrazide (504±10 mg) with 5-methylcarboxamide-10,20-bis-(2,6-difluorophenyl)porphyrin (VIII) (100±10 mg), potassium carbonate (374±10 mg) and pyridine (15 mL) or alternatively without solvent under inert atmosphere and heating between 100° C. and 150° C., for 2 hours. After cooling to room temperature, DCM (=50 mL) was added and the organic layer washed with hydrochloric acid solution (0.1 M) (3 times) and water (3 times). The organic phase was dried with anhydrous sodium sulfate, filtered and then concentrated. The solid was dissolved in ethyl acetate (20 mL) and a solution of chloranil (0.6 equiv.) in ethyl acetate (5 mL) was added. The final solution was kept under stirring at 45° C. The reaction was stopped when the UV-Vis absorption peak of bacteriochlorin (≈740 nm) had disappeared. The solvent was evaporated and the crude was dissolved in DCM (50 mL) and then washed with a saturated solution of sodium bicarbonate, with distilled water, and then dried over anhydrous sodium sulfate. The solvent was evaporated and purified by column chromatography with silica gel (DCM). The 5-methylcarboxamide-10,20-bis-(2,6-difluorophenyl)chlorin containing the two isomers (formula Xa and Xb), shown in FIG. 2, was obtained with 80±5% yield (80±5 mg). The NMR and MS of the isolated product are as follows:

Formula Xa:
$^{1}$H-NMR (400 MHz, (CD$_3$)CO) δ(ppm): −1.89 (s, 1H, NH); −1.59 (s, 1H, NH); 3.34 (d, J=4.6 Hz, 3H, CH$_3$); 4.33-4.37 (m, 2H, β-H); 4.76-4.80 (m, 2H, β-H); 7.49-7.55 (m, 4H, Ar—H); 7.89-7.99 (m, 2H, Ar—H); 8.29 (bs, 1H, NH) 8.44 (d, J=4.4 Hz, 1H, β-H); 8.48 (d, J=4.4 Hz, 1H, β-H); 8.82 (d, J=4.2 Hz, 1H, β-H); 8.99 (d, J=4.5 Hz, 1H, β-H); 9.06 (d, J=4.2 Hz, 1H, β-H); 9.25 (s, 1H, meso-H); 9.27 (d, J=4.5 Hz, 1H, β-H).
$^{19}$F NMR: (376.5 MHz, (CD$_3$)$_2$CO) δ ppm: −110.47 (s, 2F, Ar—F); −111.53 (s, 2F, Ar—F).
MS ESI-FIA-TOF: Calculated for (C$_{34}$H$_2$F$_4$N$_5$O) [M+H]$^+$: 594.1911, obtained [M+H]$^+$: 594.1911.

Formula Xb:
$^{1}$H-NMR (400 MHz, (CD$_3$)CO) δ(ppm): −1.79 (s, 1H, NH); −1.63 (s, 1H, NH); 3.37 (d, J=4.6 Hz, 3H, CH$_3$); 4.33-4.37 (m, 2H, β-H); 4.68-4.72 (m, 2H, β-H); 7.50-7.56 (m, 4H, Ar—H); 7.90-8.04 (m, 3H, Ar-H+NH); 8.46 (d, J=4.4 Hz, 1H, β-H); 8.52 (d, J=4.2 Hz, 1H, β-H); 8.83 (d, J=4.6 Hz, 1H, β-H); 8.97 (d, J=4.6 Hz, 1H, β-H); 9.05 (d, J=4.3 Hz, 1H, β-H); 9.37 (d, J=4.4 Hz, 1H, β-H); 10.05 (s, 1H, meso-H).
$^{19}$F NMR: (376.5 MHz, (CD$_3$)$_2$CO) δ ppm: −110.47 (s, 2F, Ar—F); −111.52 (s, 2F, Ar—F).
MS ESI-FIA-TOF: Calculated for (C$_{34}$H$_2$F$_4$N$_5$O) [M+H]$^+$: 594.1911, obtained [M+H]$^+$: 594.1912.

Example 2. Procedures for the Preparation of 5-methylcarboxamide-10,20-bis-(2,6-difluorophenyl)bacteriochlorin Solid State Method:
The synthesis of 5-methylcarboxamide-10,20-bis-(2,6-difluorophenyl)bacteriochlorin (IX) was performed by reaction of p-toluenesulphonyl hydrazide (2.52±0.05 g) with 5-methylcarboxamide-10,20-bis-(2,6-difluorophenyl)porphyrin (0.2±0.05 g), at pressure below 6×10$^{-1}$ mbar, under heating (140±1° C.) for 60 minutes. After cooling to room temperature the reaction crude was dissolved and purified by chromatography. The 5-methylcarboxamide-10,20-bis-(2,6-difluorophenyl)bacteriochlorin was obtained with 80±5% yield (160±20 mg).

Solvent Method:
The synthesis of 5-methylcarboxamide-10,20-bis-(2,6-difluorophenyl)bacteriochlorin (IX) was performed by reaction of p-toluenesulphonyl hydrazide (12.5±0.05 g) with 5-methylcarboxamide-10,20-bis(2,6-difluorophenyl)porphyrin (1±0.05 g), potassium carbonate (4.6±0.05 g), 2-methylpyridine (20 mL) and toluene (40 mL) under inert atmosphere and heating (110±2° C.) for 3 hours. After cooling to room temperature, DCM (≈400 mL) was added and sequentially washed with a solution of hydrochloric acid (0.1 M) (3 times), water (3 times), sodium hydroxide (0.05 M) (3 times) and water (3 times). The organic phase was dried with anhydrous sodium sulfate, filtrated and then concentrated. The solvent was evaporated and purified by chromatography. The 5-methylcarboxamide-10,20-bis-(2,6-difluorophenyl)bacteriochlorin was obtained with 75±5% yield (750±50 mg).

Figure 3:
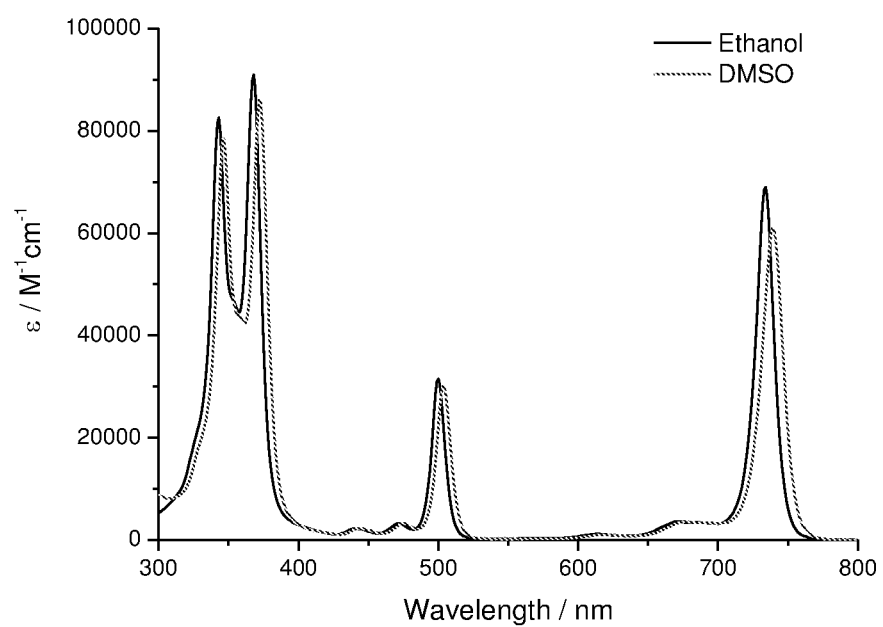
FIG. 3: Absorption spectra of the molecule of formula (IX) in ethanol and DMSO.

The absorption spectra of IX in ethanol and DMSO are presented in FIG. 3. The NMR, MS and EA of the isolated product are as follows:
$^{1}$H-NMR (400 MHz, (CD$_3$)CO) δ(ppm): −1.52 (s, 1H, NH); −1.56 (s, 1H, NH); 3.30 (d, J=4.7 Hz, 3H, CH$_3$); 4.11-4.16 (m, 4H, β-H); 4.43-4.45 (m, 2H, β-H); 4.53-4.57 (m, 2H, β-H); 7.44-7.48 (m, 4H, Ar—H); 7.81-7.90 (m, 3H, Ar-H+NH); 8.14-8.16 (m, 1H, β-H); 8.22-8.23 (m, 1H, β-H); 8.63-8.65 (m, 1H, β-H); 8.78-8.80 (m, 1H, β-H); 8.94 (s, 1H, meso-H).
$^{19}$F NMR: (376.5 MHz, (CD$_3$)$_2$CO) δ ppm: −110.70 (s, 2F, Ar—F); −111.76 (s, 2F, Ar—F).
MS ESI-FIA-TOF: Calculated for (C$_{34}$H$_{26}$F$_4$N$_5$O) [M+H]$^+$: 596.2066, obtained [M+H]$^+$: 596.2057.
Elemental Analysis (C$_{34}$H$_{26}$F$_4$N$_5$O.½(H$_2$O)): calcd. C, 67.37, H, 4.33, N, 11.58, found C, 67.37, H, 4.13, N, 10.99.

Figure 4:
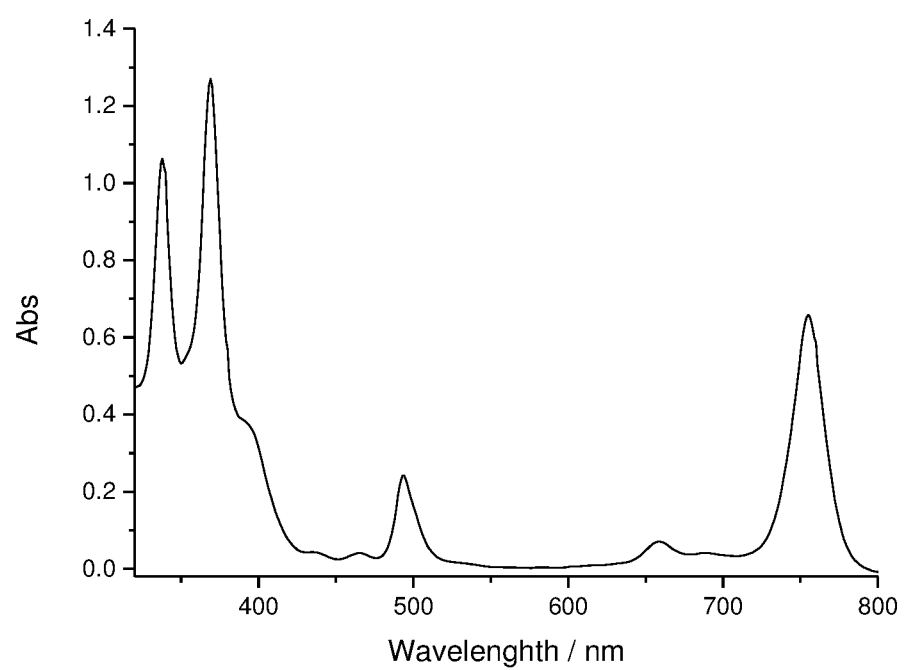
FIG. 4: Absorption spectra of the molecule of formula (XIV) in diclorometane.

Example 3. Procedure for the Preparation of 5-methylcarboxamide-10,20-bis-(trifluoromethyl)bacteriochlorin The synthesis of 5-methylcarboxamide-10,20-bis-(trifluoromethyl)bacteriochlorin (Formula XIV) was performed, using the synthetic and purification conditions of the Solvent Method described in Example 2. The absorption spectrum of XIV in dichloromethane is presented in FIG. 4. The NMR characterization of the isolated product is as follow:
$^{1}$H NMR: (400 MHz, CDCl$_3$) δ ppm: −1.00 (s, 1H, NH); −1.07 (s, 1H, NH); 3.30 (d, J=4.7 Hz, 3H, CH$_3$); 4.44-4.48 (m, 2H, β-H); 4.52-4.55 (m, 2H, β-H); 4.61-4.65 (m, 2H, β-H); 8.05 (bs, 1H, —NH); 8.75-8.76 (m, 1H, β-H); 8.84-8.86 (m, 1H, β-H); 8.96 (bs, 2H, β-H+meso-H); 9.03-9.05 (m, 1H, β-H).

Figure 5:
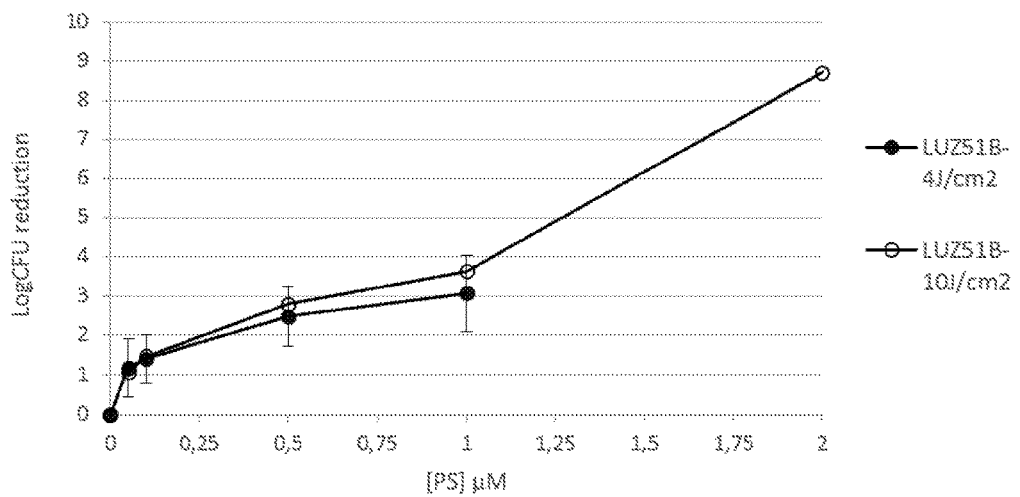
FIG. 5: Phototoxicity of the molecule of formula (IX) against *Propionibacterium acnes* after illumination with 4 J/cm$^2$ or with 10 J/cm$^2$.

Example 4. In Vitro Phototoxicity Towards *Propionibacterium acnes* after Light Irradiation This example describes the evaluation of in vitro phototoxicity of a carboxamide bacteriochlorin with formula IX after light irradiation, and their potential for PDT application in the treatment of acne vulgaris. The phototoxicity was measured according to the description in the Materials and Methods section. The n-octanol:PBS partition ratio of IX is $P_{OW}$=2.9±0.5. An adequate formulation for this carboxamide bacteriochlorin is PEG400:DMSO (55:45). The phototoxicity of the test compound is proportional to the inhibition of *P. acnes* viability relative to the non-treated control, and is represented in FIG. 5 in the form of CFU reduction as a function of photosensitizer concentration for the light doses of 4 and 10 J/cm$^2$.

Figure 6:
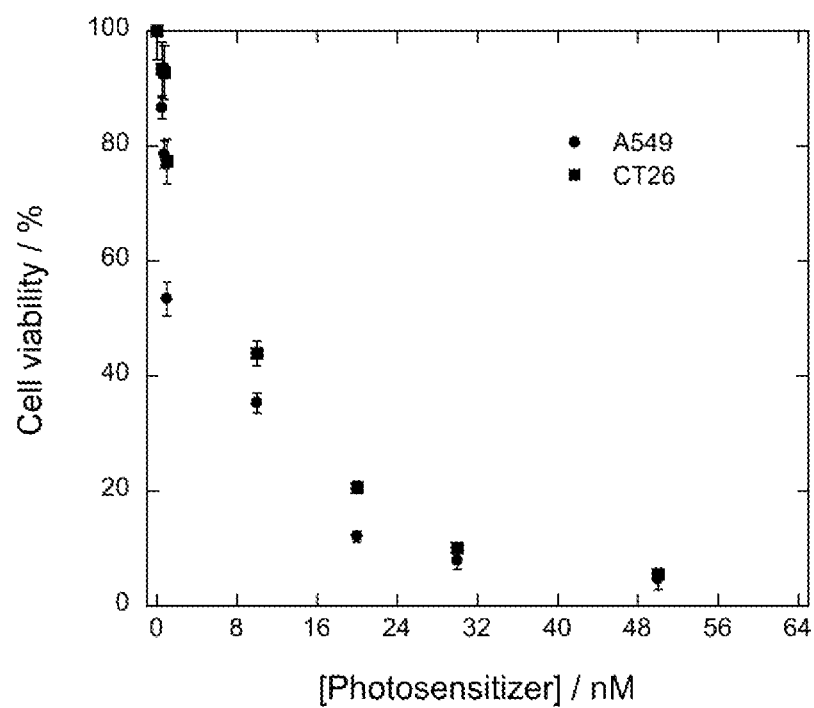
FIG. 6: Phototoxicity of the molecule of formula (IX) against cancer lines A549 and CT26 after irradiation (1 J/cm$^2$).

Example 5. In Vitro Phototoxicity Towards A549 and CT26 Cancer Cell Lines after Light Irradiation This example describes the evaluation of in vitro phototoxicity of a carboxamide bacteriochlorin with formula IX after light irradiation, and their potential for PDT of cancer. The formulation employed was the same as that of Example 4. The incubation in the dark, for 30 min, of the test compound with the A549 or CT26 cell line showed no signs of toxicity up to 40 µM. The phototoxicity was measured according to the description in the Materials and Methods section. The phototoxicity of the test compound was assessed in terms of the percentage of survival of the cells for various concentrations of the test compound incubated for 30 min, followed by washings with PBS, addition of the culture medium and illumination with a light dose of 1 J/cm². FIG. 6 shows that nearly all cells are killed when the concentration of the photosensitizer reaches 50 nM.

Figure 7:
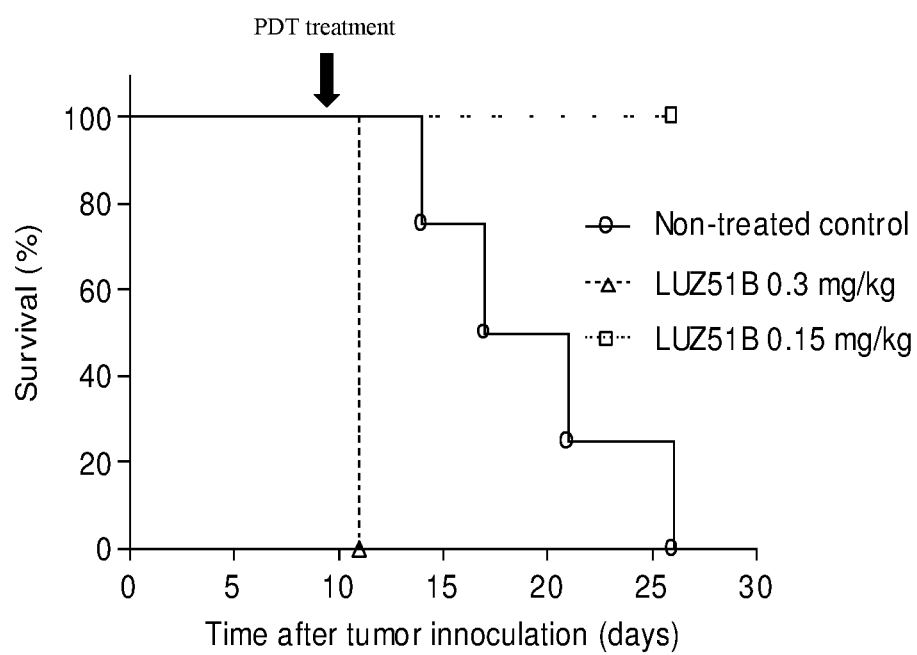
FIG. 7. Kaplan-Meier survival curves for mice with subcutaneously implanted CT26 tumors, where the solid line represents the non-treated control group, the dashed line is the group treated with 0.3 mg/kg of the molecule of formula (IX) and the dotted line is group treated with 0.15 mg/kg of the molecule of formula (IX).

Example 6. In Vivo Antitumor PDT Efficacy Against CT26 Subcutaneous Tumors Implanted in Balb/C Mice This example describes PDT of mice bearing CT26 subcutaneous tumors implanted in the right thigh. The tumors were treated with the carboxamide bacteriochlorin with formula IX using a vascular protocol when the largest diameter of the tumor reached 5 mm. The treatment protocol consisted in the intravenous injection of a defined dose of the photosensitizer with formula IX in a formulation composed of Kolliphor EL:ethanol:NaCl 0.9% (0.6:3:96.4, v/v/v), followed 15 minutes later by the illumination of the tumor with 749±3 nm laser light. The Materials and Methods section describes the animal model and the laser and optic fiber used in the treatments. The optic fiber was positioned perpendicularly to the tumor surface, in order to illuminate an area of 1.33 cm², concentric with the tumor, to deliver a light dose of 40 J/cm² with an irradiance of 130 mW/cm². The doses of the carboxamide bacteriochlorin with formula IX administered were calculated taking into account the purity of the sample. After PDT, the mice were followed to evaluate their response to the therapy until their tumor maximum diameter reached 15 mm. At this point (humanitarian endpoint) the animals were sacrificed. The efficacy results are presented as Kaplan-Meier survival curves in FIG. 7. This example shows that the photosensitizers disclosed in this work are extremely phototoxic. Indeed, the photosensitizer dose of 0.3 mg/kg was so phototoxic that the animals died of acute response to the treatment less than 72 h post-PDT. The photosensitizer dose of 0.15 mg/kg used in another treatment group was very well tolerated. The local response in the illuminated area, in the days following PDT, showed the edema and erythema related to the onset of the acute inflammatory response, accompanied by destruction of the tumor and formation of a necrotic scab. Once the necrotic scab was resolved, it was possible to see that the tumor had a complete regression and a 100% cure was achieved. On the other hand, the tumors grew continuously in the control (untreated group) and all the animals had to be sacrificed within 27 days of the tumor inoculation. The survival curve of the group treated with the 0.15 mg/kg photosensitizer dose is statistically different from that of the non-treated control group, which presents a median survival time of 19 days (Log-rank test, p<0.05).

Example 7. Skin Permeation

This example describes the permeation of carboxamide bacteriochlorin with formula IX in pig skin. The topical formulation and the animal model were described in the Materials and Methods section. The permeation was assessed both in terms of the amount of photosensitizer in the skin after designated times of contact between the topical formulation and the skin (incubation time) and in terms of the depth of the permeation in the skin.

The assessment of the amount of carboxamide bacteriochlorin with formula IX in the skin after various incubation times involved the following steps: (i) application of 0.30 ml of formulation in 1 cm² areas of minipig skin to make 6 independent measurements for the incubation times of 30, 60 and 120 minutes; (ii) cleaning of the surface of the skin at the end of the incubation times; (iii) cutting the skin in small pieces and maceration in 2 ml of dichloromethane with the aid of dispersing machine; (iv) extraction with 10 ml of dichloromethane in a falcon tube for six hours; (v) dilution by a factor of 5 with ethanol. The volume of 200 µl of the test solution was added in triplicate to 96 well plate and fluorescence intensity was detected using a Synergy HT microplate reader form Biotek (California, USA), with an excitation filter of 508/20 nm and emission filter of 760/35 nm, against a calibration curve. The signal of a blank obtained with the same cleaning method was subtracted from the signal of the sample and the concentration of the photosensitizer in each sample was obtained with the calibration curve. A summary of the results can be seen in Table 2. The flux of the photosensitizer to the skin attains $J_{max}=4\times 10^{-8}$ mol/(cm² h) in 1.5 hours, which is surprisingly high for a photosensitizer with MW=594 Da. This example shows that the low-molecular weight carboxamide derivatives of halogenated chlorins and bacteriochlorins disclosed in this work are especially capable of crossing biological barriers.

Figure 8:
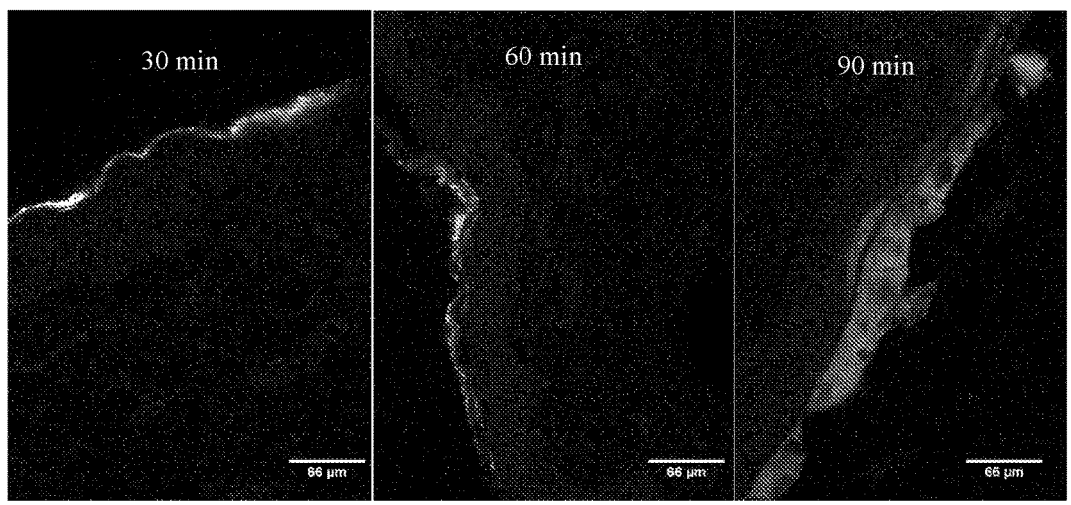
FIG. 8. Confocal microscopy of skin samples, cut perpendicular to the surface of the skin, exposed with incubation times of 30, 60 and 90 minutes to topical formulations containing the molecule of formula (IX), where the clearer regions reveal the fluorescence of the photosensitizer in the skin.

The assessment of the depth of the permeation of carboxamide bacteriochlorin with formula IX in the skin after various incubation times involved the following steps: (i) biopsies of tissues incubated with the formulation for 30, 60 and 120 minutes were collected frozen in dry ice; (ii) the frozen tissues were mounted on a holder with Tissue-Tek O.C.T. Compound (Sakura Finetek Europe B.V., Zoeterwoude, Netherlands) and cut in slices with thicknesses of 25 µm in a cryostat; (iii) the skin slices were collected in microscope slides and kept refrigerated for microscopy. Confocal fluorescence of the bacteriochlorin was performed with a LSM 510 Meta (Carl Zeiss, Jena, Germany) confocal microscope, with a ×63 oil immersion objective (Plan-Apochromat, 1.4 NA; Carl Zeiss), using $\lambda_{ex}=514$ nm, $\lambda_{em}\geq 650$ nm, laser power at 5% and an amplification 40×. Images illustrating the fluorescence of the photosensitizer in the skin after the various incubation times are presented in FIG. 8. The control experiments performed in the same conditions but without incubation of the formulation with the skin do not show any fluorescence and in the conditions of FIG. 8 are completely black. Increasing the incubation time leads to a deeper penetration of the photosensitizer in the skin that may reach 40 µm depth in 90 minutes and cover most of the epidermis. This example shows that that the low-molecular weight carboxamide derivatives of halogenated chlorins and bacteriochlorins disclosed in this work are especially capable of diffusing in biological tissues and rapidly reach their targets.

TABLE 2

Amount of carboxamide bacteriochlorin with formula IX in the skin after various incubation times.

| Experiment | Incubation time (min) | Concentration (M) | Concentration average (M) | Mass ($\mu g/cm^2$) |
|---|---|---|---|---|
| #1 | 30 | 7.26E−07 | 9.09E−07 | 5.41 ± 1.33 |
| #2 | 30 | 7.26E−07 | | |
| #3 | 30 | 4.97E−07 | | |
| #4 | 30 | 8.35E−07 | | |
| #5 | 30 | 6.68E−07 | | |
| #6 | 30 | 2.00E−06 | | |
| #1 | 60 | 1.06E−06 | 3.34E−06 | 19.9 ± 5.12 |
| #2 | 60 | 2.73E−06 | | |
| #3 | 60 | 9.14E−07 | | |
| #4 | 60 | 4.20E−06 | | |
| #5 | 60 | 5.40E−06 | | |
| #6 | 60 | 5.73E−06 | | |
| #1 | 120 | 3.35E−06 | 6.26E−06 | 37.2 ± 7.45 |
| #2 | 120 | 2.18E−06 | | |
| #3 | 120 | 6.16E−06 | | |
| #4 | 120 | 7.03E−06 | | |
| #5 | 120 | 8.53E−06 | | |
| #6 | 120 | 1.02E−05 | | |

Naturally, the present embodiments are not in any way limited to the embodiments and examples described in this document and a person with average knowledge in the field will be able to predict many possible changes to it without deviating from the main idea, as described in the claims.

DOCUMENTS CITED

1. A. N. Bashkatov, E. A. Genina, V. I. Kochubey, V. V. Tuchin, Optical properties of human skin, subcutaneous and mucous tissues in the wavelength range from 400 to 2000 nm. *J. Phys. D: Appl. Phys.* 38, 2543-2555 (2005).
2. P. Agostinis, K. Berg, K. A. Cengel, T. H. Foster, A. W. Girotti, S. O. Gollnick, S. M. Hahn, M. R. Hamblin, A. Juzeniene, D. Kessel, M. Korbelik, J. Moan, P. Mroz, D. Nowis, J. Piette, B. C. Wilson, J. Golab, Photodynamic therapy of cancer: An update. *CA Cancer J. Clin.* 61, 250-281 (2011).
3. M. R. Hamblin, T. Hasan, Photodynamic therapy: a new antimicrobial approach to infectious disease? *Photochem. Photobiol. Sci.* 3, 436-450 (2004).
4. L. Huang, M. Krayer, J. G. Roubil, Y. Y. Huang, D. Holten, J. S. Lindsey, M. R. Hamblin, Stable synthetic mono-substituted cationic bacteriochlorins mediate selective broad-spectrum photoinactivation of drug-resistant pathogens at nanomolar concentrations. *J. Photochem. Photobiol. B: Biol.* 141, 119-127 (2014).
5. N. Dragicevic-Curic, S. Winter, M. Stupar, J. Milic, D. Krajisnik, B. Gitter, A. Fahr, Temoporfin-loaded liposomal gels: Viscoelastic properties and in vitro skin penetration. *Int. J. Pharm.* 373, 77-84 (2009).
6. B. M. Magnusson, Y. G. Anissimov, S. E. Cross, M. S. Roberts, Molecular size as the main determinant of solute maximum flux across the skin. *J. Invest. Dermatol.* 122, 993-999 (2004).
7. H. A. Benson, Transdermal drug delivery: permeation enhancement techniques. *Curr. Drug Deliv.* 2, 23-33 (2005).
8. L. G. Arnaut, M. M. Pereira, J. M. Dabrowski, E. F. Silva, F. A. Schaberle, A. R. Abreu, L. B. Rocha, M. M. Barsan, K. Urbanska, G. Stochel, C. M. Brett, Photodynamic therapy efficacy enhanced by dynamics: the role of charge transfer and photostability in the selection of photosensitizers. *Chem. Eur. J.* 20, 5346-5357 (2014).
9a. S. G. Dimagno, V. S. Y. Lin, M. J. Therien, Facile elaboration of porphyrins via metal-mediated cross-coupling. *J. Org. Chem.* 58, 5983-5993 (1993).
9b. D. Fan, M. Taniguchi, Z. Yao, S. Dhanalekshmi, J. S. Lindsey, 1,9-Bis(N,N-dimethylaminomethyl)dipyrromethanes in the synthesis of porphyrins bearing one or two meso substituents. *Tetrahedron* 61, 10291-10302 (2005).
10. J. S. Lindsey, I. C. Schreiman, H. C. Hsu, P. C. Kearney, A. M. Marguerettaz, Rothemund and Adler-Longo reactions revisited: Synthesis of tetraphenylporphyrins under equilibrium conditions. *J. Org. Chem.* 52, 827-836 (1987).
11. A. D. Adler, L. Sklar, F. R. Longo, J. D. Finarelli, M. G. Finarelli, A mechanistic study of the synthesis of meso-tetraphenylporpyrin. *J. Heterocycl. Chem* 669-678, (1968).
12. M. Ptaszek, D. Lahaye, M. Krayer, C. Muthiah, J. S. Lindsey, De novo synthesis of long-wavelength absorbing chlorin-13,15-dicarboximides. *J. Org. Chem.* 75, 1659-1673 (2010).

The invention claimed is:

1. Carboxamide halogenated porphyrin derivatives, in particular bacteriochlorin or chlorin, of formula:

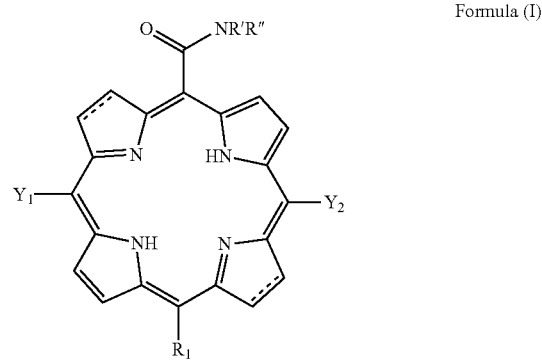

Formula (I)

wherein:
=== represents a carbon-carbon single bond or a carbon-carbon double bond, provided that at least one === represents a carbon-carbon single bond;
$Y_1$, $Y_2$ are each independently selected from the group consisting of hydrogen, halogenated alkyl, halogenated cycloalkyl with 6 or less carbon atoms, and halogenated phenyl wherein the halogens are independently selected from the group consisting of F, Cl, and Br, provided that at least one position of the alkyl, cycloalkyl or pheny is halogenated, and provided that at least one of $Y_1$, $Y_2$ is halogenated alkyl or halogenated cycloalkyl with 6 or less carbon atoms, or halogenated phenyl wherein the halogens are independently selected from the group consisting of F, Cl and Br, provided that at least one position of the alkyl, cycloalkyl or phenyl is halogenated;
$R_1$ is selected from the group consisting of H, I, Cl, Br and —CONR'R";
R' and R" are independently selected from the group consisting of hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether or ester;
or pharmaceutically acceptable salts thereof.

2. Carboxamide porphyrin derivatives according to claim 1, in particular bacteriochlorins, of formula:

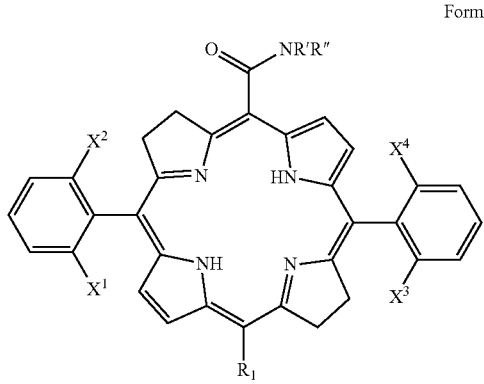

Formula (II)

wherein:
$X^1$, $X^2$, $X^3$, $X^4$ are each independently selected from the group consisting of F, Cl, Br and hydrogen atoms, provided that at least $X^1$ and $X^3$ are halogens;
$R_1$ is hydrogen;
R' and R" are independently selected from the group consisting of hydrogen, alkyl with 3 or less carbon atoms, cyclopropyl, alcohol, primary amine, secondary amine, tertiary amine, positively-charged quaternary amine, carboxylic acid, ether, or ester;
or pharmaceutically acceptable salts thereof.

3. Carboxamide porphyrin derivatives according to claim 2, wherein Formula (II):
$X^1$ and $X^3$ are fluorine atoms;
$X^2$ and $X^4$ are hydrogen atoms;
$R_1$ is hydrogen;
R', R" are independently selected from the group consisting of hydrogen and alkyl with 3 or less carbon atoms.

4. Atropisomer of the carboxamide porphyrin derivatives according to claim 2, wherein in Formula (II):
$X^1$ and $X^3$ are fluorine atoms;
$X^2$ and $X^4$ are hydrogen atoms;
$R_1$ is hydrogen;
R', R" are independently selected from the group consisting of hydrogen and alkyl with 3 or less carbon atoms;
where the fluorine atoms are on the same side of the plane defined by the macrocycle.

5. Atropisomer of the carboxamide porphyrin derivatives according to claim 2, wherein Formula (II):
$X^1$ and $X^3$ are fluorine atoms;
$X^2$ and $X^4$ are hydrogen atoms;
$R_1$ is hydrogen;
R', R" are independently selected from the group consisting of hydrogen and alkyl with 3 or less carbon atoms;
where the fluorine atoms are on opposite side of the plane defined by the macrocycle.

6. Carboxamide porphyrin derivatives according to claim 2, wherein in Formula (II):
$X^1$, $X^2$, $X^3$, and $X^4$ are fluorine atoms;
$R_1$ is hydrogen;
R' is hydrogen,
R" is methyl.

7. Carboxamide porphyrin derivatives according to claim 1, wherein the chlorins have a formula:

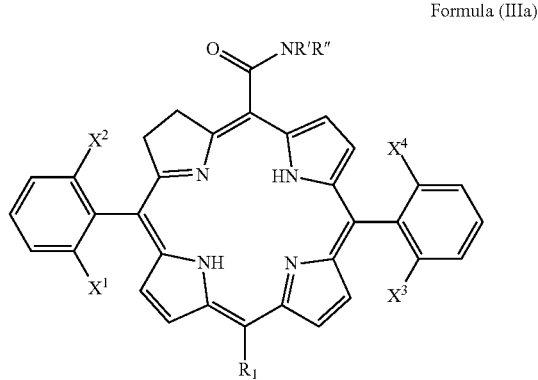

Formula (IIIa)

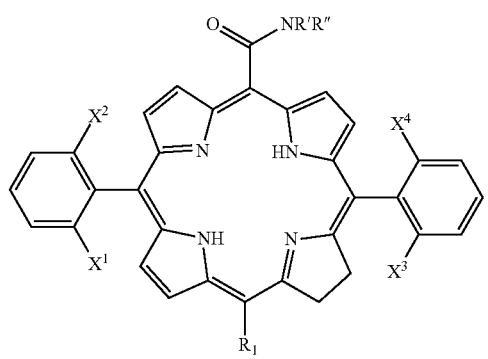

Formula (IIIb)

wherein:
$X^1$, $X^2$, $X^3$, $X^4$ are each independently selected from the group consisting of F, Cl, Br and hydrogen atoms, provided that at least $X^1$ and $X^3$ are halogens;
$R_1$ is hydrogen;
R' and R" are independently selected from the group consisting of hydrogen, alkyl with 3 or less carbon atoms, cyclopropyl, alcohol, primary amine, secondary amine, tertiary amine, positively-charged quaternary amine, carboxylic acid, ether or ester.

8. Carboxamide porphyrin derivatives according to claim 7, wherein in Formula (IIIa) or Formula (IIIb):
$X^1$ and $X^3$ are fluorine atoms;
$X^2$ and $X^4$ are hydrogen atoms;
$R_1$ is hydrogen;
R', R" are independently selected from the group consisting of hydrogen and alkyl with 3 or less carbon atoms.

9. Atropisomer of the carboxamide porphyrin derivatives according to claim 7, wherein in Formula (IIIa) or Formula (IIIb):
$X^1$ and $X^3$ are fluorine atoms;
$X^2$ and $X^4$ are hydrogen atoms;
$R_1$ is hydrogen;
R', R" are independently selected from the group consisting of hydrogen and alkyl with 3 or less carbon atoms;
where the fluorine atoms are on the same side of the plane defined by the macrocycle.

10. Atropisomer of the carboxamide porphyrin derivatives according to claim 7, wherein in Formula (IIIa) or Formula (IIIb):
$X^1$ and $X^3$ are fluorine atoms;
$X^2$ and $X^4$ are hydrogen atoms;

$R_1$ is hydrogen;

R', R" are independently selected from the group consisting of hydrogen and alkyl with 3 or less carbon atoms; where the fluorine atoms are on opposite sides of the plane defined by the macrocycle.

11. Carboxamide porphyrin derivatives according to claim 1, in particular bacteriochlorins, of formula:

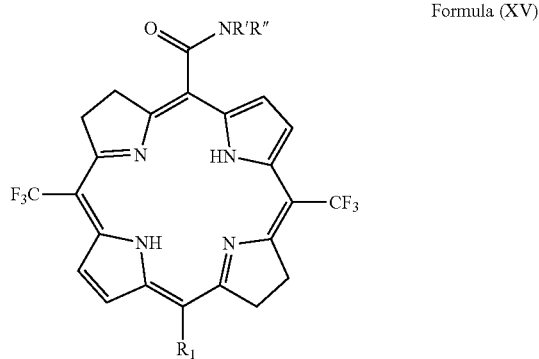

Formula (XV)

wherein:

$R_1$ is selected from the group consisting of H, Cl, Br and —CONR'R";

R' and R" are independently selected from the group consisting of hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether and ester;

or pharmaceutically acceptable salts thereof.

12. Carboxamide porphyrin derivatives according to claim 11, wherein in Formula (XV):

$R_1$ is hydrogen;
R' is hydrogen
R" is methyl.

13. Carboxamide porphyrin derivatives according to claim 1, in particular bacteriochlorins, of formula:

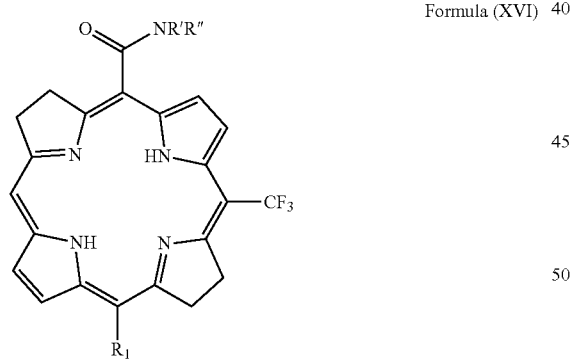

Formula (XVI)

wherein:

$R_1$ is selected from the group consisting of H, Cl, Br, and —CONR'R";

R' and R" are selected from the group consisting of hydrogen, alkyl with 6 or less carbon atoms, cyclopropyl, cyclobutyl, cyclopentyl, alcohol, primary amine, secondary amine, tertiary amine, positively-charged quaternary amine, carboxylic acid, ether and ester;

or pharmaceutically acceptable salts thereof.

14. Carboxamide porphyrin derivatives according to claim 13, wherein in Formula (XVI):

$R_1$ is hydrogen;
R' is hydrogen
R" is methyl.

15. A pharmaceutical composition comprising at least one of the carboxamide porphyrin derivatives described in claim 1 and a pharmaceutically acceptable carrier.

16. A pharmaceutically composition according to claim 15, wherein the carrier transiently permeabilizes skin and the pharmaceutical composition is permeable through the various layers of skin.

17. A method of using the carboxamide porphyrin derivatives of claim 1 for imaging target tissue comprising administering to an organism the carboxamide porphyrin derivatives of claim 1, exposing a target tissue to a magnetic field and collecting a signal using Magnetic Reasoning Imaging (MRI).

18. A method of using the carboxamide porphyrin derivatives of claim 1 for imaging target tissue comprising administering to an organism the carboxamide porphyrin derivatives of claim 1, exposing a target tissue to a light pulse of picosecond or nanosecond duration and collecting a signal using photoacoustic tomography.

19. A method of using the carboxamide porphyrin derivatives of claim 1 for imaging target tissue comprising administering to an organism the carboxamide porphyrin derivatives of claim 1, exposing a target tissue to a light source and collecting a signal using fluorescence imaging.

* * * * *